United States Patent
Farmer (12)

(10) Patent No.: US 6,733,751 B2
(45) Date of Patent: May 11, 2004

(54) USE OF EMU OIL AND ITS VARIOUS FRACTIONS AS A CARRIER FOR ANTIFUNGAL, ANTIBACTERIAL, AND ANTIVIRAL MEDICATIONS & PREPARATIONS

(75) Inventor: Sean Farmer, La Jolla, CA (US)

(73) Assignee: Ganeden Biotech, Inc., San Diego, CA (US)

(*) Notice: Subject to any disclaimer, the term of this patent is extended or adjusted under 35 U.S.C. 154(b) by 0 days.

(21) Appl. No.: 10/384,840

(22) Filed: Mar. 10, 2003

(65) Prior Publication Data

US 2003/0170334 A1 Sep. 11, 2003

Related U.S. Application Data

(62) Division of application No. 09/850,466, filed on May 7, 2001, now Pat. No. 6,531,126, which is a continuation of application No. 09/384,043, filed on Aug. 26, 1999, now abandoned.

(51) Int. Cl.$^7$ .................... A61K 35/00; A61K 31/74; A61K 39/07; A61K 35/12; A01N 25/34

(52) U.S. Cl. .................... 424/115; 424/78.07; 424/404; 424/246.1; 424/522; 514/887

(58) Field of Search .................... 424/115, 78.07, 424/78.02, 404, 246.1, 522; 514/887

(56) References Cited

U.S. PATENT DOCUMENTS

| | | | |
|---|---|---|---|
| 4,062,943 | A | 12/1977 | Lindberg |
| 4,110,477 | A | 8/1978 | Naruse et al. |
| 5,079,164 | A | 1/1992 | Kirkovits et al. |
| 5,176,911 | A | 1/1993 | Tosi et al. |
| 5,431,924 | A | 7/1995 | Ghosh et al. |
| 5,439,678 | A | 8/1995 | Dobrogosz et al. |
| 5,472,713 | A | 12/1995 | Fein |
| 5,698,227 | A | 12/1997 | Rivlin |
| 5,744,128 | A | 4/1998 | Holick |
| 5,849,334 | A | 12/1998 | Rivlin |
| 6,083,536 | A | 7/2000 | Macrides et al. |
| 6,103,246 | A | 8/2000 | Tisdale |

FOREIGN PATENT DOCUMENTS

| | | |
|---|---|---|
| HU | 12252 | 9/1976 |
| HU | 16101 | 2/1979 |
| WO | WO93/14187 | 7/1993 |
| WO | WO94/11492 | 5/1994 |
| WO | WO97/09992 | 3/1997 |
| WO | WO98/33474 A1 | 8/1998 |
| WO | WO98/47374 | 12/1998 |

OTHER PUBLICATIONS

Zemtsov et al., "Moisturizing and cosmetic properties of emu oil: A pilot double blind study", Australasian J. Dermatol. 37:159–162, 1996.

Whitehouse et al., "Emu oil(s): a source of non–toxic transdermal anti–inflammatory agents in aboriginal medicine", Inflammopharmacology 6:1–8, 1998.

Hodges et al., "Potential biocontrol of sclerotina homeocarpa and bipolaris sorokiniana on the phylloplane of Poa pratensis with strains of Pseudomonas sp.", Plant Path., 43:500–506, 1994.

Borokov et al., Mikrobn. Metab. Ikj. Ispol'z. Sel'sk. Khoz. (1973), Editors: Voznyakovskaya et al. Inst. S–kh. Mikrobiol.: Leningrad, USSR.

Murray et al., "Inhibition of fungal spore germination by gramicidin S and its potential use as a biocontrol against funal plant pathogens," Lett. Appl. Microbiol. (196) 3:5–7.

Sussman, et al., 1986. Clinical manifestations and therapy of *Lactobacillus endocarditis*: report of a case and review of the literature. Rev. Infect. Dis. 8: 771–776.*

Hata, et al., 1988. Meningitis caused by Bifidobacterium in an infant. Pediatr. Infect. Dis. 7: 669–671.*

Reid, et al., 1990. Is there a role for lactobacilli in prevention of urogenital and intestinal infections? Clin. Microbiol. Rev. 3: 335–344.*

Gibson, et al., 1995. Selective stimulation of bifidobacteria in the human colon by oligofructose and inulin. Gastroenterology 106: 975–982.*

(List continued on next page.)

Primary Examiner—Christopher R. Tate
Assistant Examiner—Michele C. Flood
(74) Attorney, Agent, or Firm—Mintz, Levin, Cohn, Ferris, Glovsky and Popeo, P.C.

(57) ABSTRACT

An animal-derived lipid is disclosed that is useful as a carrying agent for anti-microbial formulations. Pharmaceutical and other preparations including Emu Oil are also described as profoundly useful components in anti-bacterial, anti-fungal, and anti-viral treatments. This lipid material is extracted from the Emu (Dromais Novae-Hollandiae), an indigenous bird of Australia and New Zealand. The present invention also discloses therapeutic compositions comprising Emu Oil in combination with an extracellular product of *Bacillus coagulans* or *Pseudomonas lindbergii* strain, comprising a supernatant or filtrate of said culture suitable for topical application to the skin or mucosal membranes of a mammal, which are utilized to inhibit the growth of bacterium, yeast, fungi, virus, and combinations thereof. Additionally, the aforementioned therapeutic composition may also include an anti-microbial, anti-mycotic, and/or anti-viral agent. The present invention also discloses methods of treatment and therapeutic systems for inhibiting the growth of bacterium, yeast, fungi, virus, and combinations thereof, by topical application of therapeutic compositions comprising Emu Oil in combination with an extracellular product of *Bacillus coagulans* or *Pseudomonas lindbergii* strain suitable for topical application to the skin or mucosal membranes of a mammal. Similarly, the aforementioned method may also employ a therapeutic composition additionally containing an anti-microbial, anti-mycotic, and/or anti-viral agent.

13 Claims, 5 Drawing Sheets

OTHER PUBLICATIONS

Saavedra, 1994. Feeding of *Bifidobacterium bifidum* and *Streptococcus thermophilus* to infants in hospital for prevention of diarrhoea and shedding of rotavirus. Lancet 344: 1046–109.*

Mitchell, 1998. Rearming in the fight against bacteria. Lancet 352: 462–463.*

Shannon, 1998. Multiple–antibiotic–resistant salmonella. Lancet 353: 490–491.*

Thomason, et al, 1991. Bacterial vaginosis: current review with indications for asymptomatic therapy. Am. J. Obstet Gynecol. 165: 1210–1217.*

Marsh, 1993. Antimicrobial strategies in the prevention of dental caries. Caries Res. 27: 72–76.*

Hill & Embil, 1986. Vaginitis: current microbiologic and clinical concepts. Can. Med. Assoc. J. 134: 321–331.*

Fuller, R., 1989. Probiotics in man and animals. J. Appl. Bacteriol. 66: 365–378.*

Nakamura, et al., 1988. Taxonomic study for *Bacillus coagulans* Hammer 1915. J. Systematic Bacterio. 38: 63–73.*

Winberg, et al., 1993. Pathogenesis of urinary tract infection–experimental studies of vaginal resistance to colonization. Ped. Nephrol. 7: 509–514.*

Goodman, et al., 1990. Drug absorption, bioavailability, and routes of administration. The Pharmacological Basis of Therapeutics, $8^{th}$ Edition. Pergamon Press, Inc. pp 5–10.*

* cited by examiner

FIG. 1

| Characteristic | *Bacillus coagulans* Response |
|---|---|
| Catalase production | Yes |
| Acid from D-Glucose | Yes |
| Acid from L-Arabinose | Variable |
| Acid from D-Xylose | Variable |
| Acid from D-Mannitol | Variable |
| Gas from Glucose | Yes |
| Hydrolysis of Casein | Variable |
| Hydrolysis of Gelatin | No |
| Hydrolysis of Starch | Yes |
| Utilization of Citrate | Variable |
| Utilization of Propionate | No |
| Deamidation of Tyrosine | No |
| Degradation of Phenylalanine | No |
| Nitrate reduced to Nitrite | Variable |
| Allatoin or Urate Required | No |

FIG. 2

| Organism | Fluconazole µg/ml | Ganeden supernatant: dilution showing 80% inhibition |
|---|---|---|
| C. albicans | .5 | 1:4 |
| C. glabrata | 8 | Resistant |
| C. parapsilosis | 2 | 1:16 |
| C. krusei | 32 | Resistant |
| T. rubrum | 1.0 | 1:512 |
| T. mentagrophytes | 8.0 | 1:32 |
| A. flavus | >64 | Resistant |
| A. fumigatus | >64 | Resistant |
| Acremonium | >64 | 1:2 |
| Scopulariopsis | .5 | Undiluted |

FIG. 3

| Infecting Microbe | Condition |
|---|---|
| *Trichophyton* species | |
| T. mentagrophytes | tinea pedis, athlete's foot |
| T. interdigitale | tinea pedis, athlete's foot |
| T. mentagrophytes | tinea versicolor, ring worm |
| T. mentagrophytes | tinea barbae, face/neck inflammation |
| T. rubrum | dermatophytosis |
| T. yaoundei | ring worm on scalp |
| *Candida* species | |
| C. albicans | systemic candidaiasis |
| C. albicans | chronic mucocutaneous candidaiasis, myositis and thymoma |
| C. albicans | yeast and mycelial phase infection |
| C. albicans | oral thrush |
| C. tropicalis | cervical yeast infection |
| *Pseudomonas aeruginosa* | opportunistic skin infections, urinary tract infections, post surgical infections |
| *Staphylococcus aureus* | opportunistic skin infections, boils, abscess, wound infections, dermatitis |
| *Staphylococcus epidermidis* | opportunistic skin infections |
| *Streptococcus pyogenes* | opportunistic skin infections, impetigo, erysipelas |
| *Streptococcus spp.* | opportunistic skin infections, wound infections |
| *Gardnerella vaginalis* | bacterial vaginosis |
| *Propionibacterium acnes* | acne |
| *Clostridium perfingens* | open-wound infections |
| Herpes Simplex Virus I or II | cold sores, genital herpes lesions |

FIG. 4

| Mycotic Pathogen | Associated Disease | Inhibition Results |
|---|---|---|
| *T. mentagrophytes* (ATCC No. 4808) | Tinea pedis (Athlete's Foot) | Excellent |
| *T. interdigitabe* (ATCC No. 9129) | Tinea pedis (Athlete's Foot) | Excellent |
| *T. mentagrophytes* (ATCC No. 36107) | Tinea versicolor (Ring Worm) | Excellent |
| *T. menagrophytes* (ATCC No. 8125) | Tinea barbae (Face & Neck Inflammation) | Good |
| *T. mentagrophytes* (ATCC No. 9533) | Tinca pedis (Athlete's Foot) | Excellent |
| *T. mentagrophytes* (ATCC No. 28187) | Tinea pedis (Athlete's Foot) | Excellent |
| *T. rubrum* (ATCC No. 18753) | Mild Dermatophytosis | Good |
| *T. yaoundei* (ATCC No. 13947) | Ring Worm, Scalp | Good |

FIG. 5

| Species | Pathology | Inhibition Results |
|---|---|---|
| *Candida abbicans* (ATCC No. 26555) | Chronic Mucocutaneous, Candidiasis, Myositis and Thymoma | Excellent |
| *C. albicans* (ATCC No. 44203) | Systemic Candidiasis | Excellent |
| *C. albicans* (ATCC No. 44807) | Yeast and Mycelial Phase | Excellent |
| *C. tropicauis* (ATCC No. 62377) | Cervical Yeast Infection | Excellent |

USE OF EMU OIL AND ITS VARIOUS FRACTIONS AS A CARRIER FOR ANTIFUNGAL, ANTIBACTERIAL, AND ANTIVIRAL MEDICATIONS & PREPARATIONS

RELATED APPLICATIONS

This application is a divisional application of U.S. Ser. No. 09/850,466, filed May 7, 2001 now U.S. Pat. No. 6,531,126, which is a continuation application of U.S. Ser. No. 09/384,043, filed Aug. 26, 1999 now abandoned, each of which are incorporated by reference in its entirety.

FIELD OF THE INVENTION

The present invention relates to compositions and methods of use for the treatment of bacterial, fungal, and viral infections of the dermis and cuticle. More specifically, the present invention relates to compositions and methods of use of Emu Oil, and it various associated fractions, in combination with the appropriate medicaments, in the treatment of bacterial, fungal, and viral infections of the dermis and cuticle. The present invention also relates to the utilization of therapeutic compositions comprised of Emu Oil in combination with a probiotic, viable Bacillus bacteria, spores, and extracellular supernatant products, as well as the extracellular product of *Pseudomonas lindbergii*, as a topical agent for the prevention and/or control of infections caused by bacterium, fungi, yeast, and virus, and combinations thereof.

BACKGROUND OF THE INVENTION

1. Emu Oil

Emu Oil, is an animal-derived lipid composition, extracted from the Emu (Dromais Novae-Hollandiae), a flightless bird part of a group called ratites (which also includes the ostrich and the kiwi), indigenous to Australia and New Zealand.

Emu Oil is extracted from a thick fat-pad on the back of the bird which putatively functions to protect the animal from the extreme temperatures in its Australian homeland. The fat is carefully extracted to prevent the formation of trans-fatty acids, wherein approximately 100 pounds of fat produces approximately 50 to 90 pounds of unrefined, pale yellow oil. The chemical composition and characteristics of Emu Oil has been quantitatively ascertained and is set forth below in Table I.

TABLE I

| Fatty Acid Composition: | |
|---|---|
| C-14:0 (Myristic): | 0.4% |
| C-16:0 (Palmitic): | 21.5% |
| C-16:1 (Palmitoleic): | 3.7% |
| C-18:0 (Stearic): | 10.6% |
| C-18:1 (Oleic): | 51.4% |
| C-18:2 (Linoleic): | 12.7% |
| C-18:3 (Linolenic): | 0.9% |
| Calculated Iodine Value: | 69.7 |
| Free Fatty Acid: | 0.33% |
| Acid Value: | 0.66% |
| Peroxide Value: | 1.53% |
| Moisture: | 0.03% |
| Refractive Index @ 40° C.: | 1.4606% |

As illustrated in Table I, when correctly extracted and processed, Emu Oil is comprised of approximately 50% to 70% monounsaturated fatty acids, with the rest being both saturated and polyunsaturated fatty acids (see e.g., *American Emu Association News*, March 1995). Emu Oil is almost purely triglyceride in nature, which makes it an almost completely neutral lipid. In addition, the monounsaturated fatty acid, oleic acid, is the largest single fatty acid component of Emu Oil. Traditional beliefs of geographically widely-separated Australian Aboriginal communities agree on the beneficial properties of Emu Oil as a natural remedy. The oral history of the Australian Aborigines indicates their use of Emu Oil for over forty thousand years to reduce pain and stiffness in sore muscles and joints, to help expedite wound healing, as a dermal protectorate from the effects of wind and sun, and in the treatment of bruised subcutaneous tissue, burns and dry skin problems. Methods of administration are quire varied. For example, Aborigines have revealed methods of treatment which included hanging an Emu skin on a tree to collect the oil, and wrapping the affected area on the individual in a freshly-killed Emu skin. However, it is believed that in both of the aforementioned scenarios, the catalyst of the suns' heat was used to liquefy the Emu fat and enhance its absorption qualities.

Documented records of the utilization of Emu Oil may be antedated well over 100 years (see e.g., Whitehouse, et al., 1996. Concerning Emu Oil and its anti-arthritic activity. *Fifth Queensland Poultry Science Symposium*, Gatton College). The use of Emu Oil was among many natural remedies adopted by settlers from the original inhabitants of Australia. The first report known was published in the Australian Post regarding experiments by Dr. Peter Gosh (Raymond Purves Bone and Joint Research Laboratories, University of Sydney at the Royal North Shore Hospital) and Dr. Michael Whitehouse (Department of Pathology, University of Adelaide), wherein the Emu Oil was required to be massaged vigorously onto the sore muscle or joint and the process repeated as often as required, hence pressure, heat and duration of rubbing were all deemed to be relevant factors.

This, although Emu Oil has been previously described, the majority of its uses or properties/characteristics is anecdotal in nature. These uses and properties include (see e.g., DuBois, 1999. *Explore Issue* 8:1–10): (i) its ability to act as a dermal penetrant and medicament carrier; (ii) its anti-inflammatory properties; (iii) its ability to act as an emollient/emulsifier; (iv) its bacteriostatic properties; (v) its low potential for irritation of the skin; (vi) its non-comedogenic properties (i.e., it does not clog up pores); and (vii) its moisturizing, wound-healing, general "anti-aging" properties. However, the quantitative information currently available almost exclusively relates to the benefits of Emu Oil as an anti-inflammatory agent for arthritis, its uses for cardiovascular health when ingested, which is similar to the use of Omega-3 fish oils to improve high-density lipoprotein (HDL) cholesterol, and its moisturizing and general "anti-aging" properties.

There is much anecdotal material available on the anti-inflammatory abilities of Emu Oil. It has been shown to reduce pain, swelling and stiffness in joints, to reduce recent bruising and muscle pain, and ease sports related muscle strains as well. Studies have shown that different Emu Oils (i.e., oils which were extracted by different methodologies, from different sources, and the like) possessed different levels of anti-inflammatory ability. The ability of Emu Oil to penetrate the stratum coneum dermal barrier and concomitantly act as a carrier, makes it highly valuable for use in therapeutic compounds in the prevention and/or treatment of a variety of conditions. This ability is believed to be primarily due to both its extremely high content of oleic acid and a total lack of indigenous phospholipids. Accordingly, Emu Oil could be combined with various medicinals or cosmetic materials to facilitate their ability to penetrate this layer of keritinized tissue in a more efficacious and cost-effective manner than the currently-utilized liposome- and iontophorisis-based technologies. For example, the ability of Emu Oil to act as a trans-dermal penetrant with respect to Ketoprofen, a well known non-steroidal, anti-inflammatory drug (NSAID) found in Actron™ and like products, was examined in a recent study performed at Auburn University. Ketoprofen is one of the proprionic acid derivative drugs, which have been utilized in numerous European countries for more than 15 years as an effective treatment for rheumatoid arthritis and osteoarthritis. Although it is available in more than 80 countries throughout the world, it did not receive approval for over-the-counter (OTC) use in the United States until 1996. Although Ketoprofen is readily absorbed, it frequently produces a number of adverse side-effects in the gastrointestinal tract when taken orally. Moreover, the oral administration of Ketoprofen has also been associated with such serious deleterious physiological side-effects as renal dysfunction, marked edema, and hepatic dysfunction (e.g., jaundice). The utilization of a topically-administered Ketoprofen composition to the dermis over the inflamed tissues or joints would perhaps mitigate some of the aforementioned side-effects and may also potentially result in the accumulation of the drug within associated synovial tissues, the site of the desired anti-inflammatory reaction. However, recent studies in which Ketoprofen was topically-administered without the utilization of dermal-penetrants (e.g., Emu Oil) demonstrated that this compound was adsorbed through viable, keritinized dermal tissue in a very limited concentration, if at all.

Conversely, the results demonstrated that the concomitant utilization of a dermal-penetrant produced markedly elevated adsorption of the compound. Specifically, an Emu Oil—propanol—Ketoprofen combination was shown to produce a 3-times higher serum levels in mice following trans-dermal application, than either a DMSO—Bovine Serum—Ketoprofen or an Isopropyl alcohol—Ketoprofen combination. This result was particularly encouraging due to the fact that Emu Oil was approved by the FDA for human use in July of 1992, and DMSO has not yet received such approval.

In a related study, the ability of Emu Oil to decrease the concentration of inflammatory molecules was examined (see Smith and Craig-Schmidt, AEA Convention Las Vegas, Nev. (Jun. 6–8, 1995)). Eicosanoids are hormone-like compounds synthesized from essential fatty acids and have been demonstrated to be synthesized in dermal tissue (see e.g., Wilkerson and Walsh, 1977. *J. Invest. Dermatol.* 68: 210–214). While some of these compounds serve normal physiological functions, others are involved in the inflammatory response. In this study, prostaglandin F2a (PGF2a.) was utilized as an indicator of ecosanoid synthesis within the dermal tissue. The topical administration of was shown to decrease ecosanoid production in skin, as reflected by suppression of PGF2a. This result may offer a possible biochemical explanation for the reported beneficial effects of topically administered Emu Oil.

Additionally, in 1995, Australian researchers isolated a component in Emu Oil which appears to be at least one of the active ingredients directly responsible the oil's anti inflammatory activity. Thus, this substance could potentially be utilized to develop or isolate additional anti inflammatory medications which are without deleterious physiological side-effects, are non-irritating, which possess long-term biological and physiological activity, and which are far less expensive than currently-utilized anti-inflammatory regimens.

Emu Oil also possesses a high degree of emollient/emulsification properties, and hence has good "blendability". In practice this means that Emu Oil has the ability to blend or make oil and water misable, producing a cream that does not feel oily on the skin. One inherent problem is that most creams do not penetrate the dermal barrier, however this is ameliorated by the utilization of Emu Oil without leaving an oily residue behind. This bodes very well for its future use in both the cosmetic and pharmaceutical industries.

An additional property of Emu Oil is that it is bacteriostatic. Recent studies have demonstrated that in its pure state, Emu Oil grows no bacterial organisms. Thus, pure non-contaminated Emu Oil has a long shelf-life due to its bacteriostatic nature and due to its low levels of polyunsaturated fats which are the most subject to oxidation and eventual rancidity. Similarly, Emu Oil's bacteriostatic activity will be of useful in both cosmetic and pharmaceutical industries.

Emu Oil also possesses an extremely low potential for irritation of the skin. Moreover, it has also been shown to have almost no side-effects, which means that (even at full strength), Emu Oil has irritation levels so low that they are the same as those found in putting water on the skin (i.e., is practically nonexistent). This characteristic is unusual, as most anti-inflammatory drugs are irritating, when applied topically, and possess side-effects.

Emu Oil is non-comedogenic in nature, and does not "clog" the pores of the skin nor tend to cause acne when used. This tendency cannot be said for, e.g., mineral oil (which is one of the current, popular carrier oils in cosmetics and rubbing oils) which frequently causes outbreaks of acne when used.

Finally, Emu Oil is a highly efficacious moisturizing agent, which adds to its protective ability and promotes anti-aging of the skin. Researchers believe that its unique combination of saturated and unsaturated fatty acids may be an explanation for its ability to enhance the willingness of the upper layers of the skin to retain water. For example, application of Emu Oil has been demonstrated to increase the overall thickness of human skin by approximately 2.5-times, thus reducing its tendency to form "wrinkles". In addition, there is much anecdotal information regarding the anti-aging and wound healing abilities of Emu Oil. A double-blind study is currently being performed at the Timothy J. Harner Burn Center (affiliated with the University Medical Center in Lubbock, Tex.) to authenticate this anecdotal material.

The general "anti-aging" properties of Emu Oil was examined at the Boston University School of Medicine. In this double-blind study, a refined Emu Oil known as Kalaya (New World Technology; Los Angeles, Calif.) was topically-administered daily to depilated mice, over a two-week time-period. Corn oil was utilized as the negative control substance. Results demonstrated that the refined Emu Oil produced a 20% increase in the overall rate of DNA synthesis within the skin cells of these animals, whereas the rate of DNA synthesis within the negative control animals remained normal. A marked increase in the overall thickness of the skin, to which the Emu Oil had been applied, was also found. In addition, over 80% of hair follicles which were quiescent at the time of the initiation of the study, were stimulated by the application of the Emu Oil and began to produce a viable hair shaft. Typically, hair follicles go through stages from a quiescent phase, to an active hair-growth phase, and back to the quiescent phase again. The administration of Emu Oil was found to not only stimulate the hair follicles into the active phase, but it kept them in this phase during the entire period of administration, as well.

Studies regarding the properties of Emu Oil have expanded to prominent noted facilities/groups including, but not limited to: Auburn University; The Arthritis Clinic, Ardmore, Okla.; Texas Technical University; Timothy J. Harnar Burn Center; and Iowa State University.

The use of Emu Oil in veterinary medicine has also gained favor (see e.g., Zimmer, 1999. *J. Equine Med.* 56: 112–117). Emu Oil is frequently used in combination with DMSO or dexamethasone, or Gentamicin for the management of wounds. The treatment of non-suturable wounds (e.g., distal leg wounds where there is decreased muscle mass), by twice-daily application of Emu Oil was shown to markedly increase epithiliazation of these wounds, while concomitantly reducing the development of necrotic tissue and scarring. Similarly, the frequency of dehiscence of sutured wounds was also demonstrated to be markedly reduced in Emu Oil-treated equines. Emu Oil in combination with NSAID is also used to control stiffness and pain in those affected joints in lame or arthritic horses. A frequent winter lesion seen in dairy cattle is frosted teat ends, wherein the teat end freezes and skin around the teat sloughs. Topical administration of Emu Oil has been found to accelerate the healing process and allows the continued milking of the cow during this process. The bacteriostatic properties of Emu Oil is also effective in the prevention and/or treatment of infections of the teat in dairy cows due to milk residues. Similarly, Emu Oil is more effective in the treatment of ringworm lesions (commonly seen in calves) than other conventional techniques (e.g., bleach, iodine preparations, and the like). Another area in which Emu Oil is utilized in veterinary medicine is the treatment of lesions or sores caused by casts. When a cast area is applied it frequently retains moisture or causes pressure on bony protuberances, resulting in the formation of dermatitis or cast sores. Following the removal of the cast, the use of Emu Oil greatly accelerates the healing process of these aforementioned sores.

2. Dermal Infections

Dermal infections, especially those caused by mycotic pathogens, make-up a considerable percentage of the sale of prescription and over-the-counter medications that are sold annually worldwide. According to the Center for Disease Control and Prevention (CDCP), there is currently a dramatic rise in the number of reported mycotic and bacterial skin infections. Annual sales of dermal and cuticular anti-fungal agents is currently exceeding two billion U.S. dollars each year. Moreover, dermal mycotic illness was recently shown to be increasing at a rate of approximately 9% to 15% per annum, depending upon the specific pathogen and disease. One of the primary factors responsible for the growth of these markets is the fact that more fungal pathogens are becoming resistant to the commonly-utilized anti-fungal agents each year. Examples of anti-fungal agents which are commonly-utilized, include, but are not limited to: Fluconazole (Diflucan®; Pfizer Pharmaceutical), Intraconazole (Sporonox®; Janssen Pharmaceutical), Miconazole Nitrate, Ketoconazole, Tolnaftate, Lamasil, Griseofulvin, Amphotercin B, and other compounds and the formulations thereof.

New generations of anti-fungal and anti-bacterial drugs and preparations are being developed every year to replace those medication in which pathogens have become resistant. As the search for more effective anti-microbial agents continues, so does the search for "carrying agents" which are utilized to disperse and facilitate penetration of these medications through the various dermal and cuticular membranes and tissues. However, to date there has been little success in finding an agent that is able to penetrate dense cuticular material such as finger/toenails and animal hooves.

Diseases that are most common to human dermal and cuticular membranes include: (i) Candidaiasis (e.g., caused by *Candida albicans, Candida tropicalis, Candida golbratta, Candida parapsilosis*); (ii) Tineal diseases, also known as Athletes Foot (Tinea Pedis), Jock Itch (Tinea Cruis), Scalp Infection (Tinea Capitis), Ring Worm, and Beard infections (Tinea Barbae), are all caused by the Trichophyton species, including, but not limited to: *Trichophyton mentagrophytes*; (iii) diseases which are caused by bacterial pathogens, including, but not limited to: *Pseudomonas aeruginosa, Staphylococcus aerues, Staphylococcus epidermidus*, and *Propionibacterium acnes*; and (iv) diseases which are caused by viral pathogens, including, but not limited to: Herpes simplex I & II, and Herpes zoster. Perhaps one of the most difficult-to-treat diseases of fungal etiology are fungal infections of the toenail or fingernail (i.e., Onychomycosis) due to the inability of the currently-available therapeutic compositions to penetrate the dermis or cuticle. The pathogen most commonly associated with this very difficult to treat disease is *Trichophyton rubrum*.

In animals, the most common dermal fungal disease is Ring Worm. In animal hooves, especially athletic equine, there are several diseases of the hoof that are potentially quite serious and difficult to treat, including: White Line Disease (also known as "Seedy Toe"), Hoof Thrush (another yeast- or Candida-related malady), and Drop Sole. In addition, Clubbed Foot is another dermal fungal disease that is of significant concern to the equine industry.

3. Bacillus coagulans

*Bacillus coagulans* is a non-pathogenic gram positive spore-forming bacteria that produces L(+) lactic acid (dextrorotatory) in homofermentation. This microorganism has been isolated from natural sources, such as heat-treated soil samples inoculated into nutrient medium (see e.g., *Bergey's Manual of Systemic Bacteriology*, Vol. 2, Sneath, P.H.A., et al., eds., (Williams & Wilkins, Baltimore, Md., 1986)). Purified *Bacillus coagulans* strains have served as a source of various enzymes including, but not limited to: restriction endonucleases (see U.S. Pat. No. 5,200,336); amylase (see U.S. Pat. No. 4,980,180); lactase (see U.S. Pat. No. 4,323,651); and cyclo-malto-dextrin glucanotransferase (see U.S. Pat. No. 5,102,800). *Bacillus coagulans* has been used to produce lactic acid (see U.S. Pat. No. 5,079,164). In addition, a strain of *Bacillus coagulans* (designated *Lactobacillus sporogenes*, Sakaguti & Nakayama (ATCC 31284)) has been combined with other lactic acid-producing bacteria and *Bacillus natto* to produce a fermented food product from steamed soybeans (see U.S. Pat. No. 4,110,477). *Bacillus coagulans* strains have also been used as animal feed additives for poultry and livestock to reduce disease and improve feed utilization and to, therefore, increase growth rate in the animals (see PCT Patent Application Nos. WO 9314187 and WO 9411492).

DESCRIPTION OF THE FIGURES

FIG. 1: illustrates various metabolic activities and the associated, characteristic physiological or biochemical response in *Bacillus coagulans*.

FIG. 2: illustrates the various pathogens, which may be treated by use of the therapeutic compositions of the present invention, and their associated disorders.

FIG. 3: illustrates, in tabular form, a comparison of the anti-mycotic, Fluconazole with *Bacillus coagulans* and *Pseudomonas lindbergii* supernatants (generically designated Ganeden Supernatant) in the inhibition of various bacterial, fungal, and yeast species.

FIG. 4: illustrates the tested fungal strains of Trichophyton species, their ATCC accession numbers, and the results of in vitro inhibition by *Bacillus coagulans*.

FIG. 5: illustrates the tested yeast pathogen strains, their ATCC accession numbers, and the results of in vitro inhibition by *Bacillus coagulans*.

SUMMARY OF THE INVENTION

The present invention discloses the discovery that numerous dermally-associated animal diseases can be mitigated and/or prevented while concomitantly maintaining dermal and cuticular health by use of a combination of active agents within a therapeutic composition which includes: anti-fungal, anti-bacterial, or anti-viral agents comprising organic molecules, proteins and carbohydrates and/or bacterial fermentation products in combination with Emu Oil and its various associated fractions. These therapeutic composition comprise the fermentation products of specific bacterial strains in combination with an effective amount of Emu Oil in a pharmaceutically-acceptable cater suitable for administration to the dermal and/or cuticular membranes of an animal.

In another embodiment of the present, the active anti-microbial agent is a quatenary ammonium chloride. In another embodiment, the active anti-microbial agent is an Iodine or iodifer compound such as Betadine™. In another embodiment, the active anti-microbial agent is a phenolic compound. In another embodiment, the active anti-microbial agent is a ethanol, isopropyl or other alcohol compound or tincture. In another embodiment, the active anti-microbial agent is a systemic anti-fungal compound such as Amphotericin B, Dapsone, Fluconazole, Flucytosine, Griseofulvin, Itraconazole, Kietoconazole, Miconazole, KI. In another embodiment, the active anti-microbial agent is a topical anti-fungal compound such as Amphotericin B, Carbol-Fuchsin, Ciclopirox, Clotrimzole, Econazole, Haloprogin, Ketoconazole, Mafenide, Miconazole, Naftifine, Nystatin, Oxiconazole, Silver Sulfadiazine, Sulconazole, Terbinafine, Tioconazole, Tolnafiate, Undecylenic acid. In another embodiment, the active anti-microbial agent is a anti-fungal vaginal compound such as Butoconazle, Clotrimazole, Econazole, Gentian Violet, Miconazole, Nystatin, Terconazole, Tioconazole.

In a preferred embodiment of the present invention, a therapeutic composition comprising an extracellular product of *Bacillus coagulans* or *Pseudomonas lindbergii* species in a pharmaceutically-acceptable carrier suitable for topical application to skin or a mucosal membrane of a mammal and Emu Oil for use in the prevention and/or control of infections caused by bacterium, fungi, yeast, and virus, and combinations thereof, is disclosed. In this preferred embodiment, the extracellular product comprises the supernatant or filtrate of a culture of a *Bacillus coagulans* or *Pseudomonas lindbergii* species.

In further embodiments of the present invention, methods for inhibiting growth of bacteria, yeast, fungus, virus or a combination thereof, are provided, and include the steps of applying topically to skin or a mucous membrane a composition comprising an extracellular product of a *Bacillus coagulans* or *Pseudomonas lindbergii* strain, and allowing the composition to be present for sufficient time to inhibit growth of bacteria, yeast, fungus, virus or any combination thereof. In one embodiment, the applying step includes applying the composition in the form of a cream, lotion, gel, oil, ointment, suspension, aerosol spray, powder, aerosol powder or semi-solid formulation.

According to yet another aspect of the invention, there is provided a composition comprising an extracellular product of a *Bacillus coagulans* or *Pseudomonas lindbergii* is applied to a flexible article that is intended to be worn by or attached to skin or a mucous membrane of a mammal to allow probiotic activity of the bacteria to occur adjacent to or on the skin or mucous membrane.

In another embodiment of the invention, there is provided a method of inhibiting growth of bacteria, yeast, fungus, virus or any combination thereof, including the steps of applying a composition comprising a Bacillus species or the extracellular product of a *Bacillus coagulans* or *Pseudomonas lindbergii* to a solid surface, contacting the solid surface to skin or a mucous membrane of a mammal, and allowing the solid surface to contact the skin or mucous membrane for sufficient time to allow initiation of probiotic activity of the isolated bacteria or anti-microbial properties of the extracellular product to inhibit growth of bacteria, yeast, fungus, virus or a combination thereof adjacent to or on the skin or mucous membrane. In one embodiment, the applying step includes applying the composition to a diaper, pliable material for wiping skin or a mucous membrane, dermal patch, adhesive tape, absorbent pad, tampon or article of clothing. In another embodiment, the applying step includes impregnating the composition into a fibrous or non-fibrous solid matrix.

The present invention also discloses a therapeutic system for treating, reducing or controlling microbial infections comprising a container comprising a label and a therapeutic composition as described herein, wherein said label comprises instructions for use of the composition for treating infection.

It should be understood that both the foregoing general description and the following detailed description are exemplary and explanatory only and are not restrictive of the invention as claimed.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated by reference.

As utilized herein, the term "probiotic" refers to microorganisms (e.g., bacteria, yeast, viruses, and/or fungi) which form, at a minimum, a part of the transient or endogenous flora and, thus, possess a beneficial prophylactic and/or therapeutic effect upon the host organism. Probiotics are generally known to be clinically-safe (i.e., non-pathogenic) by those skilled within the art. Although not wishing to be bound by any particular mechanism, the probiotic activity of Bacillus species is thought to result from competitive inhibition of growth of pathogens due to superior colonization, parasitism of undesirable microorganisms, lactic acid production and/or other extracellular products having anti-microbial activity, or combinations thereof.

As utilized herein, the term "microbial" refers to bacteria, yeast, fungi, and/or virus.

The present invention discloses therapeutic compositions, methods of use, and articles of manufacture of a therapeutic composition comprising an extracellular product of *Bacillus coagulans* or *Pseudomonas lindbergii* species in a pharmaceutically-acceptable carrier suitable for topical application to skin or a mucosal membrane of a mammal and Emu Oil for use in the prevention and/or control of infections caused by bacterium, fungi, yeast, and virus, and combinations thereof, is disclosed. In this preferred embodiment, the extracellular product comprises the supernatant or filtrate of a culture of a *Bacillus coagulans* or *Pseudomonas lindbergii* species.

1. Lactic Acid-Producing Bacterial Strains

Typical lactic acid-producing bacteria useful as a probiotic of this invention are efficient lactic acid producers which include non-pathogenic members of the Bacillus genus which produce bacteriocins or other compounds which inhibit the growth of pathogenic organisms. Exemplary lactic acid-producing, non-pathogenic Bacillus species include, but are not limited to: *Bacillus coagulans; Bacillus coagulans* Hammer; and *Bacillus brevis* subspecies coagulans.

Exemplary lactic acid-producing Lactobacillus species include, but are not limited to: *Lactobacillus acidophilus, Lactobacillus casei*, Lactobacillus DDS-1, Lactobacillus GG, *Lactobacillus rhamnosus, Lactobacillus plantarum, Lactobacillus reuteri, Lactobacillus gasserii, Lactobacillus jensenii, Lactobacillus delbruekii, Lactobacillus, bulgaricus, Lactobacillus salivarius* and *Lactobacillus sporogenes* (also designated as *Bacillus coagulans*).

Exemplary lactic acid-producing Sporolactobacillus species include all Sporolactobacillus species, for example, Sporolactobacillus P44.

Exemplary lactic acid-producing Bifidiobacterium species include, but are not limited to: *Bifidiobacterium adolescentis, Bifidiobacterium animalis, Bifidiobacterium bifidum, Bifidiobacterium bifidus, Bifidiobacterium breve, Bifidiobacterium infantis, Bifidiobacterium infantus, Bifidiobacterium longum*, and any genetic variants thereof.

Several Bacillus species which are preferred in the practice of the present invention, include, but are not limited to the lactic acid-producing *Bacillus coagulans* and *Bacillus laevolacticus*. Additionally, probiotic *Bacillus coagulans* is non-pathogenic and is generally regarded as safe (i.e., GRAS classification) by the U.S. Federal Drug Administration (FDA) and the U.S. Department of Agriculture (USDA), and by those individuals skilled within the art. Various other non-lactic acid-producing Bacillus species may be utilized in the present invention so long as they produce compounds which possess the ability to inhibit pathogenic bacterial or mycotic growth. Examples of such suitable non-lactic acid-producing Bacillus include, but are not limited to: *Bacillus subtilis, Bacillus uniflagellatus, Bacillus lateropsorus, Bacillus laterosporus* BOD, *Bacillus megaterium, Bacillus polymyxa, Bacillus licheniformis, Bacillus pumilus*, and *Bacillus sterothermophilus*. Other strains that could be employed due to probiotic activity include members of the Streptococcus (Enterococcus) genus. For example, *Enterococcus faecium*, is commonly used as a livestock probiotic and, thus, could be utilized as a co-administration agent. It should be noted that, although exemplary of the present invention, *Bacillus coagulans* is only utilized herein as a model for various other acid-producing (e.g., lactic acid) species of lactic acid-producing bacteria which may be useful in the practice of the present invention, and therefore is not to be considered as limiting.

The growth of these various Bacillus species is generally well-known within the art. It should be noted that the exemplary culture and preparative methods which are described herein for *Bacillus coagulans* may be readily utilized and/or modified for growth and preparation of the other lactic acid-producing bacteria disclosed in the present invention.

2. *Bacillus coagulans*

Although, as disclosed herein, any of the aforementioned Bacillus strains may be utilized in the practice of the present invention, purified *Bacillus coagulans* is exemplary and preferred as a probiotic for biological control of various microbial pathogens. Because *Bacillus coagulans* forms heat-resistant spores, it is particularly useful for making pharmaceutical compositions for treating microbial infections. Topical formulations which include viable *Bacillus coagulans* spores in a pharmaceutically-acceptable carrier, are particularly preferred for making and using preventive and therapeutic compositions of the present invention. The term "topical" is broadly utilized herein to include both epidermal and/or skin surfaces, as well as mucosal surfaces of the body.

2.1 Characteristics and Sources of *Bacillus coagulans*

The Gram positive rods of *Bacillus coagulans* have a cell diameter of greater than 1.0 $\mu$m with variable swelling of the sporangium, without parasporal crystal production. *Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., *Bergey's Manual of Systemic Bacteriology*, Vol. 2, Sneath, P. H. A. et al., eds., Williams & Wilkins, Baltimore, Md., 1986). Purified *Bacillus coagulans* strains have served as a source of enzymes including endonucleases (e.g., U.S. Pat. No. 5,200, 336); amylase (U.S. Pat. No. 4,980,180); lactase (U.S. Pat. No. 4,323,651) and cyclo-malto-dextrin glucano-transferase (U.S. Pat. No. 5,102,800). *Bacillus coagulans* has also been utilized to produce lactic acid (U.S. Pat. No. 5,079,164). A strain of *Bacillus coagulans* (also referred to as *Lactobacillus sporogenes*; Sakaguti & Nakayama, ATCC No. 31284) has been combined with other lactic acid producing bacteria and *Bacillus natto* to produce a fermented food product from steamed soybeans (U.S. Pat. No. 4,110,477). *Bacillus coagulans* strains have also been used as animal feeds additives for poultry and livestock to reduce disease and improve feed utilization and, therefore, to increase growth rate in the animals (International PCT Patent Applications No. WO 9314187 and No. WO 9411492). In particular, *Bacillus coagulans* strains have been used as general nutritional supplements and agents to control constipation and diarrhea in humans and animals.

Purified *Bacillus coagulans* bacteria utilized in the present invention are available from the American Type Culture Collection (ATCC, Rockville, Md.) using the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284); and *Bacillus coagulans* Hammer NCA 4259 (ATCC No. 15949). Purified *Bacillus coagulans* bacteria are also available from the Deutsche Sarumlung von Mikroorganismen und Zellkuturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384, corresponds to ATCC No. 11369); and *Bacillus coagulans* Hammer (DSM No. 2385, corresponds to ATCC No. 15949). *Bacillus coagulans* bacteria can also be obtained from commercial suppliers such as Sabinsa Corporation (Piscataway, N.J.) or K.K. Fermentation (Kyoto, Japan).

*Bacillus coagulans* strains and their growth requirements have been described previously (see e.g., Baker, D. et al, 1960. *Can. J. Microbiol.* 6: 557–563; Nakamura, H. et al, 1988. *Int. J. Syst. Bacteriol.* 38: 63–73. In addition, various strains of *Bacillus coagulans* can also be isolated from natural sources (e.g., heat-treated soil samples) using well-known procedures (see e.g., *Bergey's Manual of Systemic Bacteriology*, Vol 2, p. 1117, Sneath, P. H. A. et al., eds., Williams & Wilkins, Baltimore, Md., 1986).

It should be noted that *Bacillus coagulans* had previously been mis-characterized as a Lactobacillus in view of the fact that, as originally described, this bacterium was labeled as *Lactobacillus sporogenes* (see Nakamura et al. 1988. *Int. J. Syst. Bacteriol.* 38: 63–73). However, initial classification was incorrect due to the fact that *Bacillus coagulans* produces spores and through metabolism excretes L(+)-lactic acid, both aspects which provide key features to its utility. Instead, these developmental and metabolic aspects required that the bacterium be classified as a lactic acid bacillus, and therefore it was re-designated. In addition, it is not generally appreciated that classic Lactobacillus species are unsuitable for colonization of the gut due to their instability in the harsh (i.e., acidic) pH environment of the bile, particularly human bile. In contrast, *Bacillus coagulans* is able to survive and colonize the gastrointestinal tract in the bile environment and even grown in this low pH range. In particular, the human bile environment is different from the bile environment of animal models, and heretofore there has not been any accurate descriptions of *Bacillus coagulans* growth in human gastrointestinal tract models.

2.2 Growth of *Bacillus coagulans*

*Bacillus coagulans* is aerobic and facultative, grown typically in nutrient broth, pH 5.7 to 6.8, containing up to 2% (by wt) NaCl, although neither NaCl nor KCI are an absolute requirement for growth. A pH value ranging from approximately pH 4 to pH 6 is optimum for initiation of sporulation. It is optimally grown at about 30° C. to about 55° C., and the spores can withstand pasteurization. It exhibits facultative and heterotrophic growth by utilizing a nitrate or sulfate source. Additional metabolic characteristics of *Bacillus coagulans* are summarized in FIG. 1.

*Bacillus coagulans* can be grown in a variety of media, although it has been found that certain growth conditions produce a culture which yields a high level of sporulation. For example, sporulation is enhanced if the culture medium includes 10 mg/liter of manganese sulfate, yielding a ratio of spores to vegetative cells of about 80:20. In addition, certain growth conditions produce a bacterial spore which contains a spectrum of metabolic enzymes particularly suited for the present invention (i.e., the control of microbial infections).

(A) Culture of Vegetative *Bacillus coagulans*

*Bacillus coagulans* is aerobic and facultative, and is typically cultured at pH 5.7 to 6.8, in a nutrient broth containing up to 2% (by wt) NaCl, although neither NaCl, nor KCl are required for growth. A pH of about 4.0 to about 7.5 is optimum for initiation of sporulation (i.e., the formation of spores). The bacteria are optimally grown at 30° C. to 45° C., and the spores can withstand pasteurization. Additionally, the bacteria exhibit facultative and heterotrophic growth by utilizing a nitrate or sulfate source.

*Bacillus coagulans* can be cultured in a variety of media, although it has been demonstrated that certain growth conditions are more efficacious at producing a culture which yields a high level of sporulation. For example, sporulation is demonstrated to be enhanced if the culture medium includes 10 mg/l of $MgSO_4$ sulfate, yielding a ratio of spores to vegetative cells of approximately 80:20. In addition, certain culture conditions produce a bacterial spore which contains a spectrum of metabolic enzymes particularly suited for the present invention (i.e., production of lactic acid and enzymes for the enhanced probiotic activity and biodegradation). Although the spores produced by these aforementioned culture conditions are preferred, various other compatible culture conditions which produce viable *Bacillus coagulans* spores may be utilized in the practice of the present invention.

Suitable media for the culture of *Bacillus coagulans* include: PDB (potato dextrose broth); TSB (tryptic soy broth); and NB (nutrient broth), which are all well-known within the field and available from a variety of sources. In one embodiment of the present invention, media supplements which contain enzymatic digests of poultry and/or fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Newark, N.J.); BBL (Cockeyesville, Md.); Advanced Microbial Systems (Shakopee, Minn.); and Troy Biologicals (Troy, Md.

In a preferred embodiment of the present invention, a culture of *Bacillus coagulans* Hammer bacteria (ATCC No. 31284) was inoculated and grown to a cell density of approximately $1 \times 10^8$ to $1 \times 10^9$ cells/ml in nutrient broth containing: 5.0 g Peptone; 3.0 g Meat Extract; 10–30 mg $MnSO_4$ and 1,000 ml distilled water, the broth was then adjusted to pH 7.0. The bacteria were cultured by utilization of a standard airlift fermentation vessel at 30° C. The range of $MnSO_4$ acceptable for sporulation was found to be 1.0 mg/l to 1.0 g/l. The vegetative bacterial cells can actively reproduce up to 65° C., and the spores are stable up to 90° C.

2.3 Extracellular Products Possessing Anti-Microbial Activity

*Bacillus coagulans* cultures contain secreted products which possess anti-microbial activity. These secreted products are useful in therapeutic compositions according to the present invention. Cell cultures are harvested as described above, and the culture supernatants are collected, by filtration or centrifugation, or both, and the resulting supernatant contains anti-microbial activity useful in the therapeutic compositions of the present invention.

The preparation of a *Bacillus coagulans* extracellular products will be more fully described in the Specific Examples section, infra.

(A) Preparation of *B. coagulans* and *P. lindbergii* Extracellular Products

One liter cultures of either *Bacillus coagulans* or *Pseudomonas lindbergii* were prepared as described supra, except that the fructo-oligosaccharide (FOS) was omitted. The culture was maintained for 5 days as described, at which time FOS was added at a concentration of 5 g/liter, and the culture was continued. Subsequently, 20 ml of carrot pulp was then added at day 7, and the culture was harvested when the culture became saturated (i.e., no substantial cell division).

The culture was first autoclaved for 30 minutes at 250° F., and then centrifuged at 4000 r.p.m. for 15 mm. The resulting supernatant was collected and filtered in a Buchner funnel through a 0.8 μm filter. The filtrate was collected and further filtered through a 0.2 μm Nalge vacuum filter. The resulting final filtrate was then collected (an approximate volume of 900 ml) to form a liquid containing an extracellular product which was to be quantitatively analyzed and utilized in the subsequent inhibition studies.

The results of these aforementioned analytical methodologies demonstrated that the culture supernatants from both *Bacillus coagulans* and *Pseudomonas lindbergii* are very heterogeneous in nature, containing a plurality of proteinaceous and organic molecules. However, the molecules which predominate are the proteins, of which there are a total of 20 distinct species in each of the samples. These protein species can be further fractionated by use of ion exchange chromatography, thus allowing additional characterization. Furthermore, there are also numerous pigmented molecules (i.e., molecules which absorb visible light) that are both highly conjugated (based upon their absorbance at high wavelengths) and hydrophobic (based upon their preference for non-polar solvents and retention on the C-18 HPLC column).

Following the aforementioned analysis and characterization, 1 ml of the aforementioned extracellular product was added to the test plate in place of the bacterium. After an identical culture time, a zone of inhibition of approximately 10 to 25 mm in diameter was observed. As designated herein, "excellent inhibition" means the zone was 10 mm or greater in diameter; and "good inhibition" means the zone was greater than 2 mm in diameter but less than 10 mm in diameter. Thus, these results illustrate the potent anti-microbial activity of the *Bacillus coagulans* extracellular product, which is of "excellent" quality using the terminology set forth above.

In an additional assay, a comparison of the anti-mycotic, Fluconazole with *Bacillus coagulans* supernatant in the inhibition of various bacterial, fungal, and yeast species, was performed. As illustrated in FIG. 2, these supernatants were effective in inhibiting a majority of the organisms against which they were tested. Serial dilutions of the *Bacillus coagulans* supernatant were performed with RPMI medium and inhibition was determined at 80% in accordance with the NCCLS standard for anti-fungal susceptibility.

Specifically, the results demonstrated that *Trichophyton rubrum* was totally inhibited by undiluted supernatant, and 1:2, 1:4, 1:8, 1:16, 1:32, 1:64, 1:128, and 1:256 serial dilutions, and the organism was 80% inhibited by the compound diluted 1:512 with RPMI medium. *Trichophyton mentagrophytes* was totally inhibited by the undiluted supernatant, and 1:2, 1:4, 1:8, and 1:16 serial dilutions, and the organism was 80% inhibited by the supernatant diluted 1:32 with RPMI medium. *Candida parapsilosis* was totally inhibited by the undiluted supernatant and 1:2, 1:4, 1:8, 1:16, 1:32, 1:64, 1:128, and 1:256 serial dilutions, and the organism was 80% inhibited by the supernatant diluted 1:16 with RPMI medium. *Candida albicans* was totally inhibited by the undiluted supernatant and a 1:2 dilution, and the organism was 80% inhibited by the supernatant diluted 1:4 with RPMI medium. Acremonium sp. was totally inhibited by the undiluted supernatant and was 80% inhibited by the supernatant diluted 1:2 with RPMI medium. Scopulariopsis sp. was 80% inhibited by the undiluted supernatant, but was uninhibited by any of the serial dilutions of the supernatant. The supernatant showed no inhibitory activity against *Candida glabrata, Candida krusel*, or the two Aspergillus species. Thus, the supernatant was demonstrated to possess marked inhibitory activity, in a wide variety of dilutions, against a majority of the tested organisms. Moreover, the *Bacillus coagulans* supernatant appeared to be extremely effective against dermatophytes (e.g., Trichophyton sp.), which are a causative organism in many mammalian dermal diseases.

In a preferred embodiment of the present invention, the liquid containing the extracellular product was formulated into a liquid ointment composition for use in direct application onto a tissue using a dropper, such as would be convenient to treat a fungal infection of the toe nail. This liquid ointment was prepared by combining the liquid extracellular product produced above with Emu Oil in a ratio of approximately 8:2, and trace fragrances were added to produce an aesthetic component.

Alternatively, one may use any liposomal or oil based transdermal delivery component in place of the Emu Oil. The typical ratio of probiotic extracellular product to carrier or delivery component is a range of from approximately 1% to 90% probiotic, and preferably is approximately 10% to 75% probiotic.

2.4 Anti-Microbial Activity of *Bacillus coagulans*

It is well-documented clinically that many species of bacterial, mycotic and yeast pathogens possess the ability to cause a variety of disorders. Therefore, the utilization of the probiotic microorganism-containing compositions of the present invention inhibits these pathogens are useful in the prophylactic or therapeutic treatment of conditions associated with infection by these aforementioned pathogens.

Pathogenic bacteria inhibited by *Bacillus coagulans* activity include, for example, *Staphylococcus aureus, Staphylococcus epidermidus, Streptococcus pyogenes, Pseudomonas aeruginosa, Escherichia coli* (i.e., enterohemorrhagic species), numerous Clostridium species (e.g., *Clostridium perfingens, Clostridium botulinum, Clostridium tributrycum, Clostridium sporogenes*, and the like); *Gardnereia vaginails; Proponbacterium acnes; Aeromonas hydrophia*; Aspergillus species; Proteus species; and Klebsiella species.

Pathogenic yeast and other fungi inhibited by *Bacillus coagulans* activity include *Candida albicans, Candida tropicalis* and *Trichophyton mentagrophytes, Trichophyton interdigitale, Trichophyton rubrum*, and *Trichophyton yaoundei*.

*Bacillus coagulans* has also been demonstrated to inhibit Herpes simplex viruses I (HSV-I; oral "cold sores" and Herpetic Whitlow) and Herpes simplex II (HSV-II; genital herpes) and Herpes zoster (shingles) infections.

These aforementioned pathogens have been associated with a variety of disorders including, but not limited to: diaper rash; oral, genital, cervical and vaginal yeast infections; toxic shock syndrome; chronic mucocutaneous candidaiasis; dermatophytosis; bacterial vaginosis; tineal fungal infections (e.g., ringworm, athlete's foot, and jock itch); scalp and nail fungal infections; superficial skin disorders (e.g., erysipelas, open-wound infections, acne, abscess, boil, eczema, dermatitis, contact dermatitis, hypersensitinitis, contact lesions, bed sores, and diabetic lesions); miscellaneous opportunistic infections; oral and genital viral lesions, and the like conditions as are well known in the art. Therefore, topical use of compositions containing the *Bacillus coagulans* active agents that inhibit these pathogens are useful in preventing or treating these conditions.

The various pathogens, which may be treated by use of the therapeutic compositions of the present invention, and their associated disorders are illustrated in FIG. 3. It should be noted, however, that the pathogens listed in FIG. 3 are set forth as examples only, and are not meant to be limiting to the types of organisms which can be treated by use of the methodologies or compositions of the present invention. Accordingly, various other skin- and mucous membrane-infecting microbes and dermatophytes can also be treated by use of the present compositions and methods disclosed herein.

The aforementioned anti-microbial activity of a therapeutic composition of the present invention will be more fully-described in the Specific Examples section, infra.

(A) Anti-Mycotic Activity of *Bacillus coagulans*

The ability of *Bacillus coagulans* to inhibit various fungal pathogens was demonstrated using an in vitro assay. In the assay, potato-dextrose plates (DIFCO®, Detroit, Mich.) were prepared using standard procedures and were inoculated individually with a confluent bed (about $1.7 \times 10^6$) of various species of the fungus Trichophyton. The tested fungal strains of Trichophyton species (available from the American Type Culture Collection (ATCC; Rockville, Md.)) and their ATCC accession numbers, as well as the results of in vitro inhibition by *Bacillus coagulans* are illustrated in FIG. 4.

Inhibition by *Bacillus coagulans* was ascertained by placing on the plate approximately $1.5 \times 10^6$ colony forming units (CFU) in 10 µl of broth or buffer, plated directly in the center of the potato-dextrose plate, with one test locus per plate. The size of each test locus was approximately 8 mm in diameter and a minimum of three tests were performed for each inhibition assay. The negative control consisted of a 10 ml volume of sterile saline solution, whereas the positive control consisted of a 10 ml volume 2% Miconazole (1-[2-(2,4-dichlorophenyl)-2-[(2,4-dichlorophenyl)methoxylmethyl-1, 11-imidazole within an inert cream.

The plates were then incubated for approximately 18 hr at 30° C., at which time the zones of inhibition were measured. As designated herein, "excellent inhibition" means the zone was 10 mm or greater in diameter; and "good inhibition" means the zone was greater than 2 mm in diameter, but less than 10 mm in diameter.

The results of the in vitro inhibition by *Bacillus coagulans* is illustrated in FIG. 4. For each of the Trichophyton species tested, the disease condition associated with an infection is indicated in column 2 of FIG. 4. For comparison, no zone of inhibition was seen with the negative control, whereas good inhibition (approximately 8.5 mm diameter, mean average of three tests) was seen with the positive control.

In one embodiment of the present invention, the extracellular product of the selected Bacillus strain (preferably *Bacillus coagulans*) and/or *Pseudomonas lindbergii* is combined with a therapeutically-effective dose of an anti-fungal agent and Emu Oil. In preferred embodiments of the present invention, the extracellular product of the aforementioned lactic acid-producing bacterial strains is combined with a therapeutic concentration of one or more anti-fungal agents, including, but not limited to: Dapsone, Fluconazole, Flucytosine, Griseofulvin, Itraconazole, Ketoconazole, Miconazole KI, Amphotericin B, Carbol-Fuchsin, Ciclopirox, Clotrimzole, Econazole, Haloprogin, Mafenide, Miconazole, Naftifine, Nystatin, Oxiconazole, Silver Sulfadiazine, Sulconazole, Terbinafine, Tioconazole, Tolnafiate, Undecylenic acid, Butoconazie, Clotrimazole, Econazole, Gentian Violet, Miconazole, Nystatin, Terconazole, and Tioconazole.

(B) Inhibition of Yeast by *Bacillus coagulans*

Similarly, the ability of *Bacillus coagulans* to inhibit various yeast pathogens was demonstrated in vitro for four species of Candida, all of which are available from the American Type Culture Collection (ATCC; Rockville, Md.). Each of the yeast pathogens and their ATCC accession numbers are illustrated in FIG. 5.

In the in vitro inhibition assay, potato-dextrose plates (DIFCO®, Detroit, Mich.) were prepared using standard procedures and were inoculated individually with a confluent bed about $1.7 \times 10^6$ of the four species of Candida. Inhibition by *Bacillus coagulans* was tested by placing on the plate about $1.5 \times 10^6$ colony forming units (CFU) in 10 µl of broth or buffer, plated directly in the center of the potato-dextrose plate with one test locus of about 8 mm in diameter per plate. A minimum of three tests were performed for each inhibition assay. The negative control consisted of a 10 µl volume of a sterile saline solution, whereas the positive control consisted of a 1 µl volume of Miconazole cream.

The plates were then incubated for approximately 18 hr at 30° C., at which time the zones of inhibition were measured. As designated herein, "excellent inhibition" means the zone was 10 mm or greater in diameter; and "good inhibition" means the zone was greater than 2 mm in diameter, but less than 10 mm in diameter.

The results of the in vitro tests are shown in FIG. 5 with the pathological conditions in humans associated with infection by the Candida species shown in column 2. As expected, no inhibition was seen with the negative control and good inhibition (approximately 8.7 mm diameter; average of three tests) was seen with the positive control.

(C) Anti-Microbial Activity of *Bacillus coagulans*

The ability of *Bacillus coagulans* to inhibit various opportunistic bacterial pathogens was quantitatively ascertained by use of an in vitro assay. This assay is part of a standardized bacterial pathogen screen (developed by the U.S. Food and Drug Administration(FDA)) and is commercially available on solid support disks (DIFCO® BACTROL® Disk Set). To perform the assay, potato-dextrose plates (DIFCO®) were initially prepared using standard procedures. The plates were then individually inoculated with each of the bacteria (approximately $1.5 \times 10^6$ CFU) to be tested, so as to form a confluent bacterial bed.

Inhibition by *Bacillus coagulans* was subsequently ascertained by placing approximately $1.5 \times 10^6$ CFU of *Bacillus coagulans* in 10 µl of broth or buffer, directly in the center of the potato-dextrose plate, with one test locus being approximately 8 mm in diameter per plate. A minimum of three test loci were used for each assay. The negative control consisted of a 10 µl volume of a sterile saline solution, whereas the positive control consisted of a 10 µl volume of glutaraldehyde. The plates were then incubated for approximately about 18 hr at 30° C., at which time the zones of inhibition were measured. As designated herein, "excellent inhibition" means the zone was 10 mm or greater in diameter; and "good inhibition" means the zone was greater than 2 mm in diameter but less than 10 mm in diameter.

As expected, no "inhibition" was seen with the negative, saline control, and excellent "inhibition" (approximately 16.2 mm diameter; average of three tests) was seen with the positive, glutaraldehyde control. For the enteric microorganisms tested, the following inhibition by *Bacillus coagulans* was found: (i) Clostridium species—excellent inhibition; (ii) *Escherichia coli*—excellent inhibition; (iii) Clostridium species—excellent inhibition, where the zone of inhibition was consistently greater than 15 mm in diameter. Similarly, excellent inhibition was also seen for the opportunistic pathogens *Pseudornonas aeruginosa*, and *Staphylococcus aereus*.

In summation, pathogenic enteric bacteria which were shown to be inhibited by *Bacillus coagulans* activity include, but are not limited to: *Staphylococcus aureus; Staphylococcus epidermidus; Streptococcus pyogenes; Pseudomonas aeruginosa; Escherichia coli* (enterohemorragic species); numerous Clostridium species (e.g., *Clostridium perfingens, Clostridium botulinum, Clostridium tributrycum, Clostridium sporogenes*, and the like); *Gardnereia vaginails; Proponbacterium aenes; Aeromonas hydrophia*; Aspergillus species; Proteus species; and Klebsiella species.

In one embodiment of the present invention, the extracellular product of the selected Bacillus strain (preferably *Bacillus coagulans*) and/or *Pseudomonas lindbergii* is combined with a therapeutically-effective dose of an antibiotic and Emu Oil. In preferred embodiments of the present invention, the extracellular product of the aforementioned lactic acid-producing bacterial strains is combined with a therapeutic concentration of one or more antibiotics, including, but not limited to: Gentamicin; Vancomycin; Oxacillin; Tetracyclines; Nitroflurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

3. Therapeutic Compositions

Compositions of the present invention which are suitable for use in preventing, treating, and/or controlling microbial infections comprise an active ingredient, specifically a *Bacillus coagulans* supernatant or filtrate of a *Bacillus coagulans* or *Pseudomonas lindbergii* culture grown to saturation and Emu Oil.

The therapeutic compositions may also include, but are not limited to the inclusion of: known antioxidants (e.g., vitamin E); buffering agents; lubricants (e.g., synthetic or natural beeswax); sunscreens (e.g., para-aminobenzoic acid); and other cosmetic agents (e.g., coloring agents, fragrances, oils, essential oils, moisturizers or drying agents). Thickening agents (e.g., polyvinylpyrrolidone, polyethylene glycol or carboxymethyicellulose) may also be added to the compositions.

In the therapeutic compositions of the present invention, the active agents are combined with a "carrier" which is physiologically compatible with the skin, membrane, or mucosal tissue of a human or animal to which it is topically administered. Specifically, in the preferred embodiment, the carrier is substantially inactive, with the exception of its intrinsic surfactant properties which are used in the production of a suspension of the active ingredients. The compositions may include other physiologically active constituents that do not interfere with the efficacy of the active agents in the composition. The carriers utilized in the therapeutic compositions of the present invention are preferably liquid or gel-based materials for use in liquid or gel formulations. The specific formulations depend, in part, upon the routes or modes of administration. Suitable liquid or gel-based carriers are well-known in the art (e.g., water, physiological salt solutions, urea, methanol, ethanol, propanol, butanol, ethylene glycol and propylene glycol, and the like). Preferably, water-based carriers are approximately neutral pH.

Suitable carriers include aqueous and oleaginous carries such as, for example, white petrolatum, isopropyl myristate, lanolin or lanolin alcohols, mineral oil, fragrant or essential oil, nasturtium extract oil, sorbitan mono-oleate, propylene glycol, cetylstearyl alcohol (together or in various combinations), hydroxypropyl cellulose (MW=100,000 to 1,000,000), detergents (e.g., polyoxyl stearate or sodium lauryl sulfate) and mixed with water to form a lotion, gel, cream or semi-solid composition. Other suitable carriers comprise water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. For example, emulsions containing water, glycerol stearate, glycerin, mineral oil, synthetic spermaceti, cetyl alcohol, butylparaben, propylparaben and methylparaben are commercially available. Preservatives may also be included in the carrier including methylparaben, propylparaben, benzyl alcohol and ethylene diamine tetraacetate salts. The composition may also include a plasticizer such as glycerol or polyethylene glycol (MW 400 to 20,000). The composition of the carrier can be varied so long as it does not interfere significantly with the pharmacological activity of the active ingredients of the therapeutic composition.

A therapeutic composition of the present invention may be formulated to be suitable for application in a variety of manners, for example, in a cream for topical application to the skin (e.g., for ringworm or athlete's foot), in a liquid for finger or toe nails (e.g., for tinea pedis), and the like. Other formulations will be readily apparent to one skilled in the art and will be discussed more fully in the Specific Examples section, infra.

3.1 The Utilization of Emu Oil as a Carrier in Therapeutic Compositions

As previously discussed supra, numerous animal-derived lipids have been examined for utilization as "carrying agents", which are used to disperse and facilitate penetration of these therapeutic compositions through the various dermal and cuticular membranes and tissues. However, prior to the disclosure contained herein, there has been little success in finding an agent that is able to penetrate dense cuticular material such as finger/toenails and animal hooves.

Disclosed herein is the use of an animal-derived lipid, Emu Oil, as a "carrying agent" to facilitate the dispersion and penetration of the therapeutic compositions of the present invention through the various dermal and cuticular membranes and tissues, and has been demonstrated to markedly increase the efficacy of anti-microbial and anti-fungal therapies. This lipid material is extracted from the Emu (Dromais Novae-Hollandiae), an indigenous bird of Australia and New Zealand. Although Emu Oil has been previously described, the uses which are detailed in these documents elaborate only its benefits as an anti-inflammatory agent for arthritis and its uses for cardiovascular health when ingested, which is similar to the use of Omega-3 fish oils to improve high-density lipoprotein (HDL) cholesterol.

Accordingly, both human and animal dermal diseases, caused by bacterial and/or mycotic dermatophytes, can be mitigated or prevented, while concomitantly maintaining dermal and cuticular health, by use of a combination of active agents in a therapeutic composition which includes anti-fungal/anti-bacterial agents (e.g., organic molecules, proteins and carbohydrates and/or bacterial fermentation products) in combination with Emu Oil. In a preferred embodiment of the present invention, a therapeutically-effective concentration of Emu Oil is combined with the fermentation products of bacteria that have been shown to produce inhibitory metabolites (e.g., *Bacillus coagulans*) and, optionally, with an anti-microbial agent (e.g., an anti-fungal or antibiotic), in a pharmaceutically-acceptable carrier suitable for administration to the dermal and/or cuticular membranes of an animal.

In one embodiment of the bacterial supernatant composition, the bacterial strain is a member of the Lactobacillus genus including, but not limited to: *Lactobacillus acidophilus, Lactobacillus plantarum, Lactobacillus salivarius, Lactobacillus delbrukil, Lactobacillus rhamnosus, Lactobacillus bulgaricus, Lactobacillus gaserli, Lactobacillus jensenii* and *Lactobacillus sporogenes*. In another embodiment, the bacterial strain is a member of the genus Enterococccus, Which include, but are not limited to: *Bacillus facium* and *Enterococccus thermophilus*. In another embodiment, the bacterial strain is a member of the Bifidiobacterium genus, which include, but are not limited to: *Bacillus longum, Bacillus infantis, Bacillus bifidus,* and *Bacillus bifidum*. In another embodiment, the bacterial strain is a member of the genus Bacillus, which include, but are not limited to: *Bacillus coagulans, Bacillus thermophilus, Bacillus laterosporus, Bacillus subtilis, Bacillus megaterium, Bacillus licheniformis, Bacillus mycoides, Bacillus pumilus, Bacillus lentus, Bacillus uniflagellatus, Bacillus cereus* and *Bacillus circulans*. In another embodiment the bacterial strain is a member of the genus Pseudomonas, which include, but are not limited to: *Pseudomonas aeruginosa, Pseudomonas putida, Pseudomonas lindbergii, Pseudomonas cepacia, Pseudomonas florescenes*, and Pseudomonas 679-2. In another embodiment of the present, the strain is a member of the genus Sporolactobacillus. In various other embodiments of the present invention, the bacterial strains which are utilized are members of the genus Micromonospora, Sporolactobacillus, Micrococcus, Berkholderia, Rhodococcus and any of the other bacteria which possess the ability to produce a metabolite that has anti-bacterial, anti-mycotic, or anti-viral activity.

In other embodiments of the present invention, the aforementioned bacterial supernatant compositions may be combined with an active anti-microbial agent which is a non-microbially-derived compound. These non-microbially-derived, anti-microbial compound may include, but are not limited to: a quartenary ammonium chloride, an iodine or iodifer compound (e.g., Betadine™), a phenolic compound, an alcohol compound or tincture (e.g., ethanol, isopropyl, and the like). In other embodiments, the non-microbially-derived, anti-microbial compound is a systemic anti-fungal compound, including, but not limited to: Amphotericin B, Dapsone, Fluconazole, Flucytosine, Griseofulvin, Itraconazole, Kietoconazole, or Miconazole KI. In other embodiments, the non-microbially-derived, anti-microbial compound is a topical anti-fungal compound, including, but not limited to: Amphotericin B, Carbol-Fuchsin, Ciclopirox, Clotrimzole, Econazole, Haloprogin, Ketoconazole, Mafenide, Miconazole, Naftifine, Nystatin, Oxiconazole, Silver Sulfadiazine, Sulconazole, Terbinafine, Tioconazole, Tolnafiate, or Undecylenic acid. In other embodiments, the non-microbially-derived, anti-microbial compound is an anti-fungal vaginal compound, including, but not limited to: Butoconazie, Clotrimazole, Econazole, Gentian Violet, Miconazole, Nystatin, Terconazole, or Tioconazole.

Specific methods for the utilization of Emu Oil-containing therapeutic compositions will be more fully described in the Specific Examples section, infra.

3.2 Therapeutic Methods for Treatment of Microbial Infections

The present invention discloses methodologies for treating, reducing, and/or controlling microbial infections in a variety of skin and mucosal membrane tissues using a therapeutic composition or therapeutic article of manufacture of this invention. Optimally the compositions effectively reduce the bacterial, yeast, fungal and/or viral titer in the treated individual, particularly at the site of application of the topical composition. For example, the pathogenic microbial titer in lesions has been demonstrated to be significantly reduced following the topical administration of the therapeutic composition of the present invention to the affected area(s) of the skin or mucous membrane. The disclosed methods of treatment also reduce symptoms of pathogenic microbial infection (e.g., pain associated with infected or microbial-caused lesions) and promote more rapid healing than would be found without said treatment.

The method of the present invention includes administration of a composition containing the active Bacillus ingredient to a human or animal to treat or prevent microbial (i.e., bacterial, yeast, fungal or viral) infection. Administration is preferably to the skin or a mucous membrane using a cream, lotion, gel, oil, ointment, suspension, aerosol spray, powder, semi-solid formulation (e.g., a suppository), or article of manufacture, all formulated so as to contain a therapeutic composition of the present invention using methods well-known in the art.

Application of the therapeutic composition of the present invention, containing the active agent effective in preventing or treating a microbial infection, generally consists of one to ten applications of a composition for a time period of one day up to one month. Applications are generally once every twelve hours and up to once every four hours. Preferably, two to four applications of the therapeutic composition per day, for one to seven days are sufficient to prevent or treat a microbial infection. For topical applications, the therapeutic compositions are preferably applied to lesions daily as soon as symptomology (e.g., pain, swelling or inflammation) is detected. The specific route, dosage, and timing of the administration will depend, in part, on the particular pathogen and/or condition being treated, as well as the extent of the condition.

Specific methods for the treatment of microbial infections will be more fully described in the Specific Examples section, infra, and include, but are not limited to, the treatment of diaper rash, vaginal yeast infection, opportunistic skin infection, meal fungal infection, superficial skin infection, acne, cold sores, genital Herpes lesions, Herpetic Whitlow, shingles, athlete's foot, and the like.

3.3 Therapeutic Systems for Treatment of Microbial Infections

The present invention further discloses a therapeutic system for treating, reducing, and/or controlling microbial infections comprising a container containing a label and a therapeutic composition of the present invention, wherein said label comprises instructions for the use of the therapeutic composition for the treatment of the infection.

For example, the therapeutic system can comprise one or more unit dosages of a therapeutic composition of the present invention. Alternatively, the system can contain bulk quantities of the therapeutic composition. The label contains instructions for using the therapeutic composition in either unit dose or in bulk forms as appropriate, and may include information regarding storage of the composition, disease indications, dosages, routes and modes of administration and the like information.

4. Articles of Manufacture

The present invention also discloses various articles of manufacture which utilize the beneficial aspects of the present invention by combination of the therapeutic composition with various medical or personal hygiene devices so as to reduce or prevent microbial infections associated with the use of these devices. The articles comprise compositions of an extracellular product of a lactic acid-producing bacterial species, Emu Oil, and, optionally, an anti-microbial agent applied to a solid surface or impregnated into a solid matrix of any device or article of manufacture that is intended to be in contact with skin or a mucous membrane. Preferably the solid surface is a flexible article than can be worn on or wiped on the skin or mucous membrane. More preferably, when the flexible item carrying the active agent is to be worn on the skin it includes a means for attaching the article to the skin such as, for example, an adhesive layer, inter-engaging hook and pile (i.e., Velcro®) connectors, or other well-known means of attachment such as ties, snap closures, elastic, buttons and the like.

Specific embodiments which include a Bacillus and/or isolated *Bacillus coagulans* active agent are diapers, towelettes (e.g., baby wipes or feminine hygiene towelettes), tampons, dermal patches, adhesive tape, absorbent pads, articles of clothing (e.g., underclothes, sleeping apparel), bath towels, wash cloths, and the like. The article may be made of fibrous woven, knitted or non-woven materials, occlusive or non-exclusive films or membranes, synthetic polymer fibers, films, membranes and foams (e.g., nylon, polytetrafluoroethylene (PTFE, such as Teflon® or Gore-Tex®), polystyrene, polycarbonate, polyvinylchloride and polysulphone). All of these forms are well-known within the art and include, for example, knitted or woven fabrics, non-woven fabrics such as felt and batting, fiber balls of cotton, rayon, cellulose or synthetic fibers and the like materials.

The Bacillus and/or *Bacillus coagulans* isolated active agent can be applied to the solid surface using any of a variety of known methods including, for example, applying a powder, spray drying the probiotic onto the material or soaking the material in a solution containing the probiotic and then using the wetted material or drying the material prior to use. Porous material may contain the Bacillus and/or the isolated active agent in the pores or interstices of the solid material. The Bacillus and/or the isolated active agent can be attached by adhesion, such as by attachment to an adhesive layer that is then applied to the skin (e.g., in a bandage or dermal patch). The Bacillus and/or the isolated active agent can be impregnated into the solid material during the manufacturing process of the flexible article (e.g., added to a synthetic composition before or during the polymerization process). The pressure and heat resistance of Bacillus spores makes them particularly suitable for incorporation into the material during manufacturing. Any of the solid materials carrying Bacillus and/or the isolated active agent can also be packaged individually or in groups, suitable for holding the treated material using standard packaging materials (e.g., in a shrink wrapper, sealed packet, protective wrapper or dispensing container suitable for holding dry or wet materials). The article of manufacture can have applied thereon any of the additional/optional components of a therapeutic composition of this invention, including carriers, salts, FOS, fragrances, and the like.

Any of a variety of methods for placing the therapeutic composition onto a subject article can be used, and therefore the invention need not be so limited. However, preferred methods include a "spray-dry" method in which the material is exposed in a low humidity chamber to an atomized mix containing a liquid composition, where the chamber is subsequently exposed to approximately 80–110° F. to dry the liquid, thereby impregnating the material of the article with the components of the composition.

A typical concentration is from approximately $1 \times 10^5$ to $1 \times 10^9$ CFU of viable bacterium or spores/$in^2$ of external surface of fibrous carrier/article material. Following drying, the article is ready for storage in a sterile package, or for direct use.

5. Specific Examples

The following examples relating to the present invention are illustrative and should not be construed as specifically limiting the invention. Moreover, such variations of the invention, now known or later developed, which would be within the purview of one skilled in the art are to be considered to fall within the scope of the present invention hereinafter claimed.

5.1 Treatment of Bacterial and Fungal Infections of the Dermis and Cuticle

As previously discussed, various lactic acid-producing bacteria (e.g., *Bacillus coagulans* and *Pseudomonas lindbergii*) have been shown to produce extracellular products that are anti-fungal in nature although all of the products that have come from these bacteria are a result of the purification of a specific active analog such as a protein, carbohydrate or organic molecule to form a new anti-fungal compound. It has been suggested that the use of a single active agent contributes to resistant species of pathogenic fungi and as a result new generations of anti-fungal compounds must be discovered in order to control these new developing species. However, the use of a bacterial supernatant in its crude or in a semi-refined state my be more effective in topical applications and may, in fact, decrease the rate of anti-fungal resistance by providing a more complex killing mechanism that is more difficult to overcome than a single chemical agent or analog.

The use of Emu Oil as a "carrier" in the therapeutic compositions of the present invention markedly enhances efficacy in the prevention and/or therapeutic treatment of fungal or bacterial infections of the dermis and cuticle in both humans and animals. These therapeutic compositions are comprised of the fermentation products of specific bacterial strains and, optionally, a commercially available antibiotic or anti-fungal agent in combination with an effective amount of Emu Oil in a pharmaceutically acceptable cater suitable for administration to the dermal and/or cuticular membranes of a human or animal.

In various embodiments of the present invention, the final form of the therapeutic composition may include, but is not limited to: a stabilized gel, a lotion, a cream, a semi-solid roll-on stick, a fluid, an aerosol, a spray powder, or an emulsion.

The overall efficacy of the therapeutic compositions of the present invention is relative to the concentration of Emu Oil which is utilized in the formulation. Specifically, it has been observed that higher percentages of Emu Oil is more effective than lower percentages. Not to be bound by any efficacious percentage, the range of Emu Oil used in a topical therapeutic composition of the present invention ranges from approximately 0.5% to 99.9%, with a more preferable range being between approximately 10% to 75%, and the most preferable range being between approximately 25% to 60%. The 0.5% to 99.9% ultimate effective range for Emu Oil concentration is due to the very small concentrations of anti-microbial compounds which are typically used in the therapeutic compositions of the present invention. For example, in a dermal application, the anti-fungal agent, Miconazole Nitrate, generally comprises only 2% of the total formulation.

In another embodiment of the present invention, the extracellular product of the selected Bacillus strain (preferably *Bacillus coagulans*) and/or *Pseudomonas lindbergii* is combined with a therapeutically-effective dose of an anti-fungal agent and Emu Oil. In preferred embodiments of the present invention, the extracellular product of the aforementioned lactic acid-producing bacterial strains is combined with a therapeutic concentration of one or more anti-fungal agents, including, but not limited to: Dapsone, Fluconazole, Flucytosine, Griseofulvin, Itraconazole, Ketoconazole, Miconazole KI, Amphotericin B, Carbol-Fuchsin, Ciclopirox, Clotrimzole, Econazole, Haloprogin, Mafenide, Miconazole, Naftifine, Nystatin, Oxiconazole, Silver Sulfadiazine, Sulconazole, Terbinafine, Tioconazole, Tolnafiate, Undecylenic acid, Butoconazle, Clotrimazole, Econazole, Gentian Violet, Miconazole, Nystatin, Terconazole, and Tioconazole.

In another embodiment of the present invention, the extracellular product of the selected Bacillus strain (preferably *Bacillus coagulans*) and/or *Pseudomonas lindbergii* is combined with a therapeutically-effective dose of an antibiotic and Emu Oil. In preferred embodiments of the present invention, the extracellular product of the aforementioned lactic acid-producing bacterial strains is combined with a therapeutic concentration of one or more antibiotics, including, but not limited to: Gentamicin; Vancomycin; Oxacillin; Tetracyclines; Nitroflurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

It should also be noted that the extracellular product of the selected Bacillus strain and/or *Pseudomonas lindbergii* and Emu Oil may be combined with antibiotic and anti-mycotic compounds within the same therapeutic composition.

The following are examples of therapeutic compositions which have been demonstrated to be effective in the mitigation of bacterial and mycotic diseases of the dermis and cuticle.

| Therapeutic Composition No. 1 | |
|---|---|
| Miconazole Nitrate, Fluconazole, Tolnaftate, Ketoconazole or Intraconazole | 2% |
| Emu Oil or Fraction Thereof | 90% |
| Emulsifier | 5% |
| Fragrance | 3% |
| Therapeutic Composition No. 2 | |
| Quaternary Ammonium Chloride, Iodine, Alcohol or Phenolic Compounds | 10% |
| Emu Oil or Fraction Thereof | 80% |
| Emulsifier | 7% |
| Fragrance | 3% |
| Therapeutic Composition No. 3 | |
| Bacterial Supernatant Composition Fermentation Products | 50% |
| Emu Oil or Fraction Thereof | 40% |
| Emulsifier | 7% |
| Fragrance | 3% |
| Therapeutic Composition No. 4 | |
| Bacterial Supernatant Composition Fermentation Products | 50% |
| Emu Oil or Fraction Thereof | 25% |
| Lavender Oil | 2% |
| Hydrosperse Oil | 20% |
| Emulsifying Agents | 3% |
| Therapeutic Composition No. 5 | |
| Antibiotic | 2% |
| Emu Oil or Fraction Thereof | 90% |
| Emulsifier | 5% |
| Fragrance | 3% |

As previously discussed, these aforementioned therapeutic compositions of the present invention may also be utilized in combination with other anti-fungal and/or anti-microbial agents, as set forth, supra. In addition, various other materials (e.g., Titanium oxide) to enhance the whitening of the toe or finger nail may also be used.

In a specific example, a therapeutic composition of the present invention, containing bacterial supernatant derived from *Bacillus coagulans*, was used to mitigate the human fungal infection, Onychomycosis. One ml of the aforementioned therapeutic composition was applied after bathing to each infected nail. Treatment resulted in a change in the green-to-yellow color of the nail within 10 days, in all individuals studied. In addition, within the first 7 days, the detritus under the nail sloughed-off and the thickness of the nail (one of the clinical manifestations of the disease) began to subside. Although the total amount of time which was required to ameliorate this disease varied between each subject, the average time required ranged from one month for superficial infections to six months for more pronounced Onychomycosis. Also, it must be taken into consideration that cosmetic appearance is an aspect of this disease that is independent of the pathology of the nail bed.

In has been demonstrated that the simultaneous anti-fungal action of the bacterial culture supernatant combined with the dermal-penetrating and healing aspects of the Emu Oil work in a synergistic manner to ameliorate the fungal infection. It is generally known that Emu Oil possess the ability to rehydrate skin cells in a way that promotes the growth of new cells. Similarly, it is quite possible that Emu Oil acts in a similar manner in human nail and cuticular tissues.

In other specific examples, a therapeutic composition of the present invention, containing bacterial supernatant derived from *Bacillus coagulans*, was also utilized to treat cases of diaper rash which were complicated with bacterial or fungal infections. Immediate (i.e., approximately 18 hours) relief of the dermal inflammation and redness was achieved, and all of the infections were completely ameliorated within 48 hours. Similar results have been observed in the use of these therapeutic compositions in the treatment of Jock itch (Tinea cruris), Ringworm, Athlete's Foot (Tinea pedis), Scalp infections (Tinea capitis), Beard infections (Tinea barbae), Candidaiasis of the dermis, toe, fingernail and vulva, and other dermal and cuticular diseases.

Various equine hoof diseases (e.g., White Line disease, Hoof Thrush, Drop Sole, and even Clubbed Foot) have also responded to the use of therapeutic compositions of the present invention, containing bacterial supernatant derived from *Bacillus coagulans*, in the same manner as Onychomycosis in humans. In addition, similar to its physiological activity in humans, Emu Oil may also function to rehydrate and stimulate new cell growth within animal hooves and other cuticular materials.

5.2 Prophylactic or Therapeutic Treatment of Athlete's Foot

For the prevention or therapeutic treatment of athlete's foot (i.e., tineal fungal infection), the—feet are washed with soap and water, dried thoroughly and a powder, cream, lotion, ointment or gel, such as those described in the above examples is applied to the entire foot area. Preferably, the formulation includes approximately 0.5% to 20% *Bacillus coagulans* supernatant or filtrate of a *Bacillus coagulans* or *Pseudomonas lindbergii* culture grown to saturation and 25% to 40% EMU Oil (vol./vol.). Daily treatments are continued as needed.

Additionally, athlete's foot may be prevented or treated by using a standard insole insert (e.g., a fabric, fiber or synthetic foam) having sprayed on the surface or impregnated therein with the *Bacillus coagulans* or *Pseudomonas lindbergii* extracellular anti-fungal product. Such treated insoles may be worn daily for up to two to three months, after which they are discarded and replaced with fresh treated insoles.

5.3 Treatment of Tineal Fungal Infections

Ringworm (tinea versicolor) is caused by localized infections of the skin of the trunk and neck by dermatophyte fungus which colonizes the outer layer of the skin resulting in generally circular patches of white, brown or pink flaking skin that are often itchy. Once ringworm is detected, the affected area and a surrounding approximately 1 to 10 cm$^2$ area is treated twice daily with a cream or lotion containing approximately 0.5% to 20% *Bacillus coagulans* supernatant or filtrate of a *Bacillus coagulans* or *Pseudomonas lindbergii* culture grown to saturation and 25% to 40% EMU Oil (vol./vol.).

For treatment of the related disorder, tinea cruris (i.e., "jock itch"), a cream, lotion, or aerosol spray containing approximately 0.5% to 20% *Bacillus coagulans* supernatant or filtrate of a *Bacillus coagulans* or *Pseudomonas lindbergii* culture grown to saturation and 25% to 40% EMU Oil (vol./vol.) is applied to the groin area to provide relief of itching, chafing, burning rash and irritation. Treatment is twice daily, generally after bathing and at bedtime, until symptoms are no longer detected.

Clothing, particularly underclothes and nightclothes that come in contact with the trunk and neck are sprayed with an aerosol containing approximately 0.5% to 20% *Bacillus coagulans* supernatant or filtrate of a *Bacillus coagulans* or *Pseudomonas lindbergii* culture grown to saturation and 25% to 40% EMU Oil (vol./vol.), so as to ameliorate the spread of the infection to additional areas of the body.

5.4 Topical Application to Prevent Diaper Rash

An aerosol spray liquid containing the *Bacillus coagulans* or *Pseudomonas lindbergii* active, extracellular agent is applied to diapers by the consumer before use. Alternatively, disposable diapers supplied from the manufacture may contain the *Bacillus coagulans* or *Pseudomonas lindbergii* active, extracellular agent impregnated into the diaper material where it would be adjacent to the child's skin when in use. In both of the aforementioned embodiments, the composition utilized contains approximately 0.5% to 20% *Bacillus coagulans* supernatant or filtrate of a *Bacillus coagulans* or *Pseudomonas lindbergii* culture grown to saturation and 25% to 40% EMU Oil (vol./vol.).

Alternatively or in addition to treating diapers with the *Bacillus coagulans* or *Pseudomonas lindbergii* active, extracellular agent, the child's skin in the diaper area can be treated with a saturated soft cloth wipe, powder, aerosol spray liquid, aerosol spray powder, lotion, cream or ointment containing approximately 0.5% to 20% *Bacillus coagulans* supernatant or filtrate of a *Bacillus coagulans* or *Pseudomonas lindbergii* culture grown to saturation and 25% to 40% EMU Oil (vol./vol.). Preferably, the aforementioned formulation is applied to the child's skin after bathing and/or when the diapers are changed.

5.5 Topical Treatment of Vaginal Yeast Infection (A) Vaginal Microecology

It is commonly known to those individuals skilled within the relevant arts that lactic acid-producing microorganisms (e.g., Lactobacillus) play an important role in the maintenance of a healthy vaginal ecology. However, the traditional methodologies utilized for the administration of these biorational materials do not address the numerous modes of infection of Candida and Gardnerella species, which can cause serious disease.

The vast majority of gynecologists are adamant regarding the risks of vaginal infections as a result of frequent bathing. Accordingly, gynecologists recommend the use of showers, rather than immersion bathing, to mitigate the probability of developing subsequent vaginal infections due to the associated disturbances of the "normal," lactic acid-producing vaginal flora.

(B) Yeast-Mediated Vaginal Infections

Yeast infections or vuvo-vaginal candidaiasis (VVC) is caused by various species of Candida (e.g., primarily *Candida albicans*). Over 85% of all women, at one time or another, suffer from vuvo-vaginal candidaiasis. For example, the market within the United States market for anti-fungal compounds which may be administered to ameliorate this disease is over $700 million dollars per year, with an associated 9–11% growth rate per annum. Moreover, each year, additional strains of these aforementioned mycotic pathogens are becoming resistant to the commonly utilized anti-fungal compounds (e.g., Ketoconazole, Miconazole, Fluconazole, and the like).

Healthy vaginal ecology is primarily dependant upon specific, indigenous lactic acid-producing microorganisms (e.g., Lactobacilli). Hence, there have been numerous attempts within the prior art to develop products and/or methodologies which will augment or re-establish these lactic acid-producing bacteria. For example, one product attempted to utilize hydrogen peroxide—($H_2O_2$) producing Lactobacilli as a vaginal suppository therapy for the amelioration of vaginal yeast infections.

Viability of the microorganisms continues to be the main difficulty in the use of Lactobacilli for vaginal supplementation, although it has been suggested by many companies that market Lactobacilli vaginal suppositories that any hardy bacterial strain is sufficient to accomplish mycotic mitigation within the vagina. However, these aforementioned companies primarily base their logic and subsequent assertions upon the fact that there are strains of Lactobacillus which are able to colonize the vagina, and since their strain is a member of the genus Lactobacillus then it should be efficacious. Unfortunately, this supposition or deduction could not be more in error. In a recent study, which examined the various indigenous species and strains of Lactobacilli which colonized the vaginas of 100 healthy women. The results demonstrated that *Lactobacillus acidophilus* was not the most common species of Lactobacillus isolated from the vaginas of these women, but rather the most common strains were found to be: *Lactobacillus jensenii; Lactobacillus gasserii; Lactobacillus salivarius*; and *Lactobacillus casei*.

This aforementioned information, in combination with recent evidence which established that hydrogen peroxide ($H_2O_2$) is a mandatory metabolic by-product for effective bio-augmentation, disproves the previous belief that any strain of Lactobacillus is equally efficacious for use in a suppository-based administration format. Thus, these facts demonstrate the continued need for the development of a product for vaginal supplementation, in combination with an efficacious method of administration, which ameliorates the potential physiological problems associated with the use of both bath products and bathing, in general.

(C) Bacterial-Mediated Vaginal Infections

Despite convincing evidence that lower reproductive tract infections possess the ability to migrate to the upper reproductive tract and produce inflammation, stimulate premature labor, and the like, some clinicians still hold to the tenant that lower reproductive tract infections and bacterial vaginosis are merely "markers" of upper reproductive tract infections.

It should be noted that bacterial vaginosis is not truly an microorganism-mediated infection, but instead a microecologic condition in which there are dramatic alterations in the endogenous vaginal microflora. Specifically, bacterial vaginosis involves a reduction in the overall number of lactic acid-producing bacterial strains, with a concomitant multi-log population increase in a characteristic set of microflora including, but not limited to: *Gardnerella vaginalis*, genital anaerobes, and mycoplasmas. Interestingly, these latter microorganisms, along with Streptococci and Coliforms, are the same species as those found in chorioamnionitis.

Additionally, bacterial vaginosis is also associated with increased concentrations of bacterial endotoxin, proteases, mucinases, sialidases, IgA proteases, and phospholipases A2 and C in the lower reproductive tract. Both observational and interventional studies have shown that the presence of bacterial vaginosis in the early stages of pregnancy is associated with pre-term delivery and in later stages of gestation, with miscarriage. These studies suggest that bacterial vaginosis is a direct cause of adverse outcomes in pregnancy, rather than simply being a surrogate marker. Studies suggest that ascending infection or abnormal lower reproductive tract microflora mediate adverse pregnancy outcomes. Similar microbe-host interactions occur in periodontal disease.

Bacterial vaginosis infections can also be mitigated by the use of lactic acid-producing (i.e., probiotic) organisms and/ or their extracellular products. As previously discussed, the cause-and-effect relationship in bacterial vaginosis is due to the reduction of lactic acid-producing bacterial strains with the resulting multi-log increases of to anaerobic microorganisms including, but not limited to, *Gardnerella vaginalis*. However, the results of a recent, 3900-woman study performed in Denmark demonstrated that absence of bacterial vaginosis was directly associated with sufficient vaginal colonization of aerobic lactic acid-producing organisms. In accord, vaginal supplementation with an effective lactic acid-producing bacterial species will serve to address the imbalance between aerobic lactic acid-producing organisms and the anaerobic species implicated in the etiology of bacterial vaginosis. Such vaginal supplementation may either be utilized prophylactically or therapeutically.

It has now been demonstrated that certain species of lactic acid-producing bacteria can be incorporated into highly alkaline, bath product compositions. These compositions would prove lethal to almost all other species of lactic acid-producing bacteria including, but not limited to: Lactobacillus, Bifidiobacterium, Enterococccus, and various other stains of vegetative cell bacteria.

Administration remains the major problematic issue of vaginal supplementation and, prior to the present invention, there was a long-felt need for an inoculation strategy which made vaginal lactic acid supplementation incidental. The administration of an adequate dose of an effective lactic acid organisms in a bath or shower product would thus address some of the vaginal problems associated with frequent and even occasional bathing, aroma-therapy, sea salt, bath powders, bath gels, bath oils and the like could contain an effective inoculation of the extracellular product of a lactic acid-producing bacteria for a vaginal application.

The mechanics of this type of administration may be explained in the following manner. After running a warm bath, the woman would add the bath product containing the therapeutic composition of the present invention to the water. The woman would sit in the bath, moving her legs to facilitate vaginal inoculation, for a total of approximately 20 minutes. Subsequently, this treatment could be repeated on the third day (e.g., in cases of acute vuvo-vaginal candidaiasis (VVC) or bacterial vaginitis (BV)), or on a "regular basis" (i.e., at-least monthly) in order to promote the continued stability of the vaginal ecology and microflora. In addition, this methodology should also prove useful in promoting general dermal health, as some species of lactic acid-producing bacteria are useful in the promotion of healthy skin.

In another embodiment, a soft, cloth towelette soaked in a solution of water, potassium sorbate, disodium EDTA, Emu Oil and containing the extracellular product from a lactic acid-producing bacterial species of the present invention may be utilized to clean the external vaginal area. Additional components to the aforementioned formulation may include DMDM hydantoin, isopropyl myristate, methylparaben, polysorbate 60, propylene glycol, propylparaben or sorbitan stearate. The disposable towelette is used to gently wipe the perivaginal area and is then discarded.

In yet another embodiment, solid vaginal suppositories or inserts containing the extracellular product from a lactic acid-producing bacterial species of the present invention and Emu Oil are utilized for mucosal treatment of *Candida abbicans* and/or *Candida tropicalis* infections. Such formulations can be made, for example, from a combination of corn starch, lactose, a metal stearate (e.g., magnesium stearate) and povidone. Typically, one to three solid inserts should be used per day while symptoms (e.g., vaginal itch and/or whitish discharge) are detected. Optimally, one insert per day, for a total of three to seven days, preferably at bedtime, is used.

In another embodiment, for an aerosol-based delivery of microparticulates, an aerosol spray may be formulated by combining the extracellular product from a lactic acid-producing bacterial species of the present invention and Emu Oil within a carrier mixture which is comprised of isopropyl myristate, approximately about 60% (w/w) SD alcohol 40-B, and isobutane as the propellant. A non-aerosol, manual pump spray also containing the extracellular product from a lactic acid-producing bacterial species of the present invention and Emu Oil in a neutral aqueous solution may also be utilized. A suitable spray formulation includes alcohol, glycerin, purified water and methylparaben, in addition to the *Bacillus coagulans* probiotic microorganism.

It should also be noted that while the mitigation of yeast infections is the primary vaginal-based utilization of *Bacillus coagulans* therapeutic compositions, these compositions have also been demonstrated to be highly effective in the treatment of non-pathogenic, non-specific dermatitis. Immersion in the therapeutic bathing compositions of the present invention allow the establishment of the probiotic *Bacillus coagulans* on the skin or mucosal membranes, which tends to mitigate dermatitis of unknown etiology.

5.6 Prevention and/or Treatment of Opportunistic Skin Infections

Opportunistic skin infections with Pseudomonas and or Staphylococcus species (i.e., typically *Pseudomonas aeruginosa, Staphylococcus epidernidus, Staphylococcus aureus*, and the like) commonly occur concomitantly with skin allergies (e.g., allergic reactions to plant irritants such as poison ivy), bed sores, diabetic lesions or other types of skin lesions. Probiotic formulations containing *Bacillus coagulans* spores (i.e., approximately $1\times10^5$ to $1\times10^{10}$/ml depending on the specific formulation and application) and/ or supernatant or filtrate containing extracellular bacteriocins produced by *Bacillus coagulans* or *Pseudomonas lindbergii* strains are highly useful in the prevention or treatment of opportunistic skin pathogens. Additionally, probiotic *Bacillus coagulans* formulations are useful in the prevention of infection with Meticillin-resistant *Staphylococcus aureus* (MRSA), particularly following injury or invasive surgical procedures. A water-in-oil or oil-in-water emulsion, cream, lotion, powder, aerosol powder, or aerosol spray containing the extracellular product from a lactic acid-producing bacterial species of the present invention and Emu Oil is used. Various suitable carriers have been previously described herein, and others are well-known within the art.

In the practice of this embodiment of the present invention, the skin is initially cleaned with soap and water and dried thoroughly. The therapeutic composition is then applied to the skin, ensuring that the composition is applied to the areas between the toes, under the breasts, under the arms, or any other areas where the skin may become moist or exhibit frictional chafing or abrasion.

In addition to treating the skin topically with an emulsion, cream, lotion, powder, aerosol powder, or aerosol spray containing *Bacillus coagulans* probiotic, the skin may be cleansed with a probiotic formulation such as described herein.

In another embodiment of the present invention, the extracellular product of the selected Bacillus strain (preferably *Bacillus coagulans*) and/or *Pseudomonas lindbergii* is combined with a therapeutically-effective dose of an antibiotic and Emu Oil. In preferred embodiments of the present invention, the extracellular product of the aforementioned lactic acid-producing bacterial strains is combined with a therapeutic concentration of one or more antibiotics, including, but not limited to: Gentamicin; Vancomycin; Oxacillin; Tetracyclines; Nitroflurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

Equivalents

From the foregoing detailed description of the specific embodiments of the present invention, it should be readily apparent that unique, improved methodologies for the prevention and/or therapeutic treatment of bacterial, fungal, yeast, and viral infections, have been disclosed herein. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For example, the final form (e.g., stabilized gel, cream, emulsification, and the like) which is selected for the therapeutic composition is believed to be a matter of routine for a person of ordinary skill in the art with knowledge of the embodiments described herein.

What is claimed is:

1. A method of inhibiting a fungal infection comprising administering to the skin or a mucous membrane of a mammal in need thereof, an effective amount of a composition comprising a culture supernatant or filtrate of a lactic acid-producing *Bacillus coagulans* bacterium, Emu oil, an a non-microbially derived anti-fungal agent.

2. The method of claim 1, wherein said composition is an emulsion, create, lotion, gel, oil, ointment, suspension, aerosol spray, powder, aerosol powder, or semi-solid formulation.

3. The method of claim 1, wherein the Emu Oil comprises approximately 0.5% to approximately 99.9%, by weight of said composition.

4. The method of claim 1, wherein the Emu Oil comprises approximately 10% to approximately 75%, by weight of said composition.

5. The method of claim 1, wherein the Emu Oil comprises approximately 25% to approximately 60%, by weight of said composition.

6. The method of claim 1, wherein the concentration of the culture supernatant or filtrate ranges from approximately 1% to approximately 90%, by weight of said composition.

7. The method of claim 1, wherein the concentration of the culture supernatant or filtrate ranges from approximately 10% to approximately 75%, by weight of said composition.

8. The method of claim 1, further comprising one or more compounds selected from a group comprising: dimethyl sulfoxide (DMSO), methylsulfonylmethane (MSM), and Lignisul MSM.

9. The method of claim 1, further comprising one or more anti-microbial agents selected from the group consisting of a quartenary ammonium chloride, an iodine or iodifer compound, a phenolic compound, an alcohol compound and an alcohol tincture.

10. The method of claim 1, wherein said fungal infection comprises one or more microbes selected from the group consisting of Candida species and Trichophyton species.

11. The method of claim 1, wherein said non-microbially derived anti-fungal agent is selected from the group consisting of a Dapsone compound, a Fluconazole compound, a Flucytosine compound, a Griseofulvin compound, an Itraconazole compound, a Ketoconazole compound, a Miconazole KI compound, an Amphotericin B compound, a Carbol-Fuchsin compound, a Ciclopirox compound, a Clotrimazole compound, an Econazole compound, an Haloprogin compound, a Mafenide compound, a Miconazole compound, a Naftifine compound, a Nystatin compound, an Oxiconazole compound, a Silver Sulfadiazine compound, a Sulconazole compound, a Terbinafine compound, a Tioconazole compound, a Tolnafiate compound, an Undecylenic acid compound, a Butoconazole compound, a Terconazole compound, and a Gentian Violet compound.

12. The method of claim 1, wherein said non-microbially derived anti-fungal agent is a Miconazole nitrate compound.

13. The method of claim 1, wherein said composition further comprises a culture supernatant or filtrate of a *Pseudomonas lindbergii* bacterium.

* * * * *